US011375878B2

(12) United States Patent
Fujita

(10) Patent No.: US 11,375,878 B2
(45) Date of Patent: Jul. 5, 2022

(54) INFORMATION PRESENTATION SYSTEM INCLUDING A FLEXIBLE TUBULAR INSERTION PORTION

(71) Applicant: OLYMPUS CORPORATION, Tokyo (JP)

(72) Inventor: Hiromasa Fujita, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 456 days.

(21) Appl. No.: 16/420,269

(22) Filed: May 23, 2019

(65) Prior Publication Data

US 2019/0274520 A1 Sep. 12, 2019

Related U.S. Application Data

(63) Continuation of application No. PCT/JP2016/085200, filed on Nov. 28, 2016.

(51) Int. Cl.
*A61B 1/00* (2006.01)
*A61B 5/00* (2006.01)
(Continued)

(52) U.S. Cl.
CPC .......... *A61B 1/00043* (2013.01); *A61B 1/005* (2013.01); *A61B 1/00045* (2013.01);
(Continued)

(58) Field of Classification Search
None
See application file for complete search history.

(56) References Cited

U.S. PATENT DOCUMENTS 7,869,859 B2 * 1/2011 Shinno .................. A61B 6/548
600/425
7,885,703 B2 * 2/2011 Miller .................... G16H 40/63
600/418

(Continued)

FOREIGN PATENT DOCUMENTS

CN 204840598 U 12/2015
JP 2002-16825 A 1/2002
(Continued)

OTHER PUBLICATIONS

English translation of International Preliminary Report on Patentability dated Jun. 10, 2019, together with the Written Opinion received in International Application No. PCT/JP2016/085200.
(Continued)

*Primary Examiner* — John P Leubecker
(74) *Attorney, Agent, or Firm* — Scully, Scott, Murphy & Presser, P.C.

(57) ABSTRACT

An information presentation system including a tubular system including a flexible tubular insertion portion configured to be inserted into an insertion subject, a storage medium configured to store a plurality of pieces of presentation information recognizable by a non-operator, a non-operator presentation display configured to present information in an output form recognizable by the non-operator and a processor including hardware, the processor configured to perform a selection of presentation information to be presented to the non-operator presentation display, and switch a presentation period of the selected presentation information to the non-operator presentation display.

16 Claims, 17 Drawing Sheets

(51) Int. Cl.
*A61B 1/005* (2006.01)
*A61B 1/05* (2006.01)
*A61B 1/04* (2006.01)

(52) U.S. Cl.
CPC ............ *A61B 1/00131* (2013.01); *A61B 1/04* (2013.01); *A61B 1/05* (2013.01); *A61B 5/743* (2013.01)

(56) References Cited

U.S. PATENT DOCUMENTS

| | | | |
|---|---|---|---|
| 9,294,732 B2* | 3/2016 | Gillette | H04N 7/18 |
| 2002/0040305 A1* | 4/2002 | Nakatsuchi | G16H 40/20 |
| | | | 705/2 |
| 2003/0026464 A1* | 2/2003 | Kamiyama | G16H 30/20 |
| | | | 382/128 |
| 2003/0055317 A1* | 3/2003 | Taniguchi | A61B 5/06 |
| | | | 600/117 |
| 2006/0202998 A1* | 9/2006 | Hirakawa | A61B 1/00009 |
| | | | 345/501 |
| 2012/0165620 A1 | 6/2012 | Tanis et al. | |
| 2012/0293641 A1* | 11/2012 | Nagamizu | A61B 1/00096 |
| | | | 348/65 |
| 2015/0332196 A1* | 11/2015 | Stiller | G16H 20/40 |
| | | | 705/2 |
| 2015/0359419 A1 | 12/2015 | Hane et al. | |
| 2016/0157803 A1* | 6/2016 | Keller | A61B 8/12 |
| | | | 600/427 |

FOREIGN PATENT DOCUMENTS

| | | |
|---|---|---|
| JP | 2007-319478 A | 12/2007 |
| JP | 2014-500538 A | 1/2014 |
| WO | 2014/129436 A1 | 8/2014 |
| WO | WO2015/044128 * | 4/2015 ............ A61B 5/055 |

OTHER PUBLICATIONS

Japanese Office Action dated Oct. 23, 2019 received in Japanese Patent Application No. 2018-552373, together with an English-language translation.

Chinese Office Action dated May 28, 2021 received in Chinese Patent Application No. 201680091183.X, together with an English-language translation.

Japanese Office Action dated Mar. 24, 2020 received in Japanese Patent Application No. 2018-552373, together with an English-language translation.

* cited by examiner

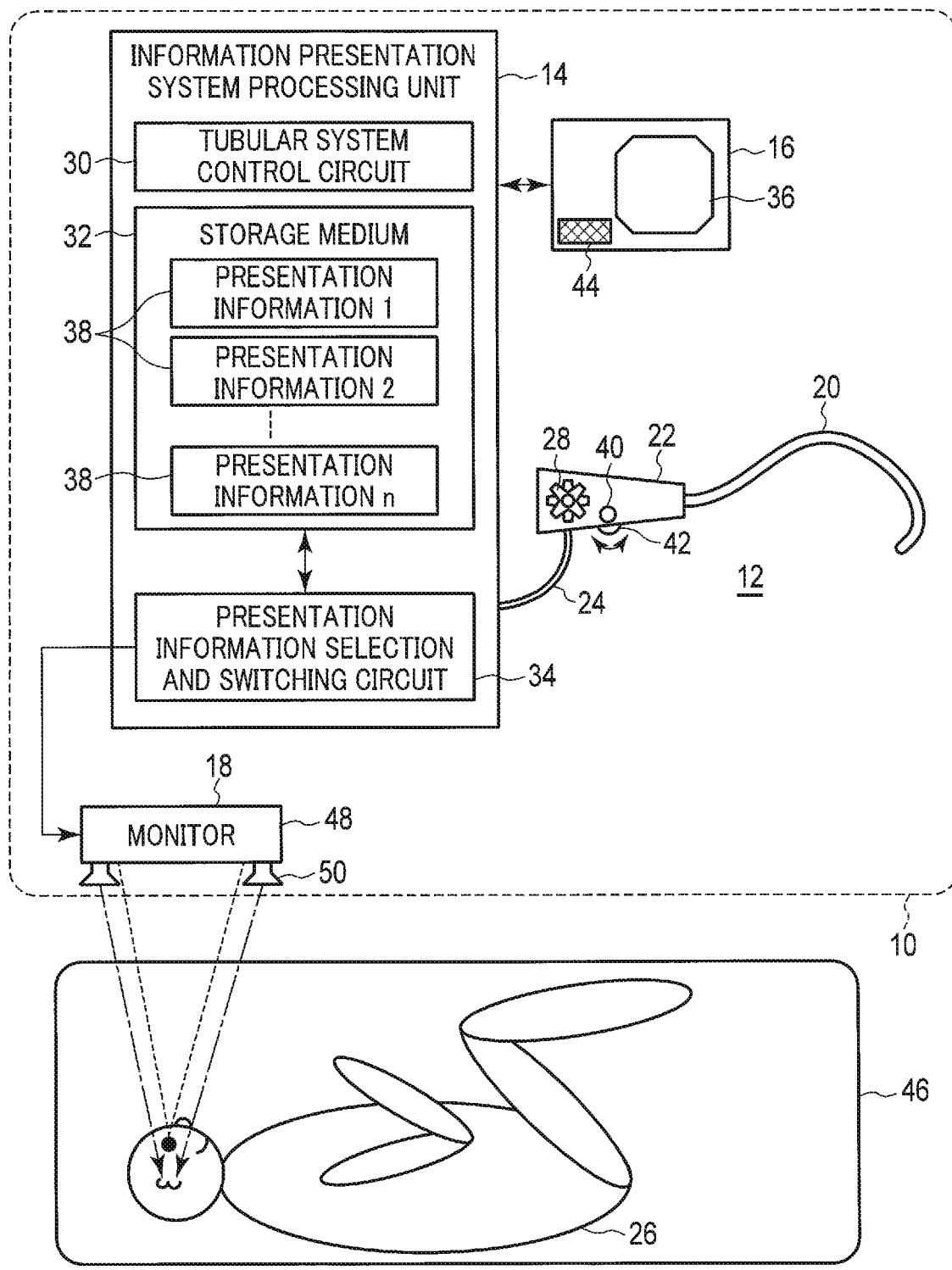
F I G. 1

| PRESENTATION INFORMATION | SPECIFIC EXAMPLE |
|---|---|
| INSERTION START | "INSERTION IS ABOUT TO START", "INSERTION WILL BE PERFORMED SAFELY, SO PLEASE RELAX", "DO NOT WORRY", ETC. |
| EXPLANATION OF HOSPITAL | EXPLANATION, SUCH AS VIDEO PROVIDING SUMMARY OF APPEAL POINTS OF INDIVIDUAL HOSPITALS |
| EXPLANATION OF OPERATOR | EXPLANATION OF CAREER, NUMBER OF INSERTIONS, DEGREE OF EXPERIENCE, ETC. |
| EXPLANATION OF EXAMINATION | EXPLANATION OF IMPORTANCE OF EXAMINATION, MERITS, ETC. |
| EXPLANATION OF INSERTION SITUATION | EXPLANATION OF LOCATION OF INSERTION PORTION IN OVERALL AREA, HOW LONG IT WILL TAKE TO COMPLETE INSERTION, ETC. EXPLANATION OF STATE OF INSERTION PORTION, ETC. EXPLANATION OF PROCEEDING TO EXAMINATION SINCE DEEPEST PORTION HAS BEEN REACHED EXPLANATION OF IMPORTANT PORTION (ENTRANCE OF CECUM OR SMALL INTESTINE, ETC.) |
| SIGN | SIGN FOR CHANGING STATE OF INSERTION SUBJECT SIDE, SUCH AS FACE-UP, LEFT-SIDEWAYS, RIGHT-SIDEWAYS, FACE-ON, BREATHE DEEPLY, HOLD BREATH, NUMBER OF WINGS OF JET ENGINE, ETC., SWITCHING OF PIPING, ETC. |
| EXPLANATION TO PROMOTE RELAXATION | "INSERTION WILL BE PERFORMED PAINLESSLY", "DO NOT WORRY", "GOING SMOOTHLY", "IT WILL NOT HURT", ETC. EXPLANATION THAT YOU CAN TAKE IT EASY, SUCH AS YOU MAY BREAK WIND OR BELCH |
| EXPLANATION OF EXAMINATION STATUS OR TREATMENT STATUS | "CLOSE EXAMINATION WILL BE PERFORMED", "LOOKS CLEAN", "NO PROBLEM", "SINCE THERE IS A POLYP, A DETAILED EXAMINATION WILL BE PERFORMED", "THIS IS NEAR THE LIVER", "THIS IS THE ANUS", ETC. |
| EXPLANATION AFTER COMPLETION | "THE DOCTOR WILL PROVIDE YOU WITH AN EXPLANATION OF THE EXAMINATION LATER. PLEASE WAIT IN THE WAITING ROOM." ETC. EXPLANATION OF EFFECT OF SEDATIVE |
| OTHERS | INFORMATION FOR NON-OPERATOR FROM HOSPITAL, ETC. |

FIG. 2

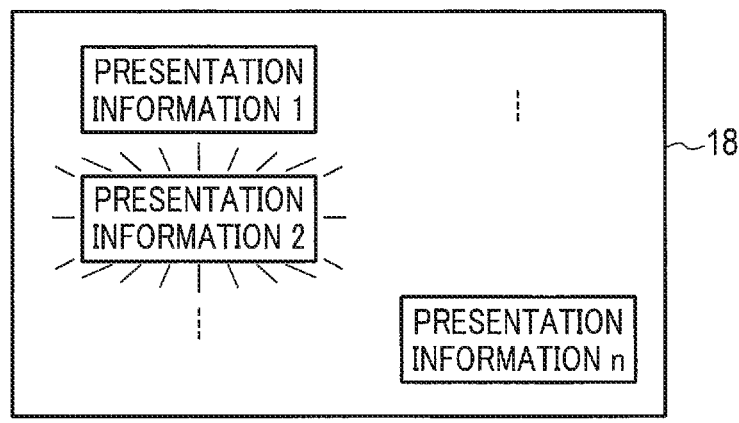
F I G. 3A
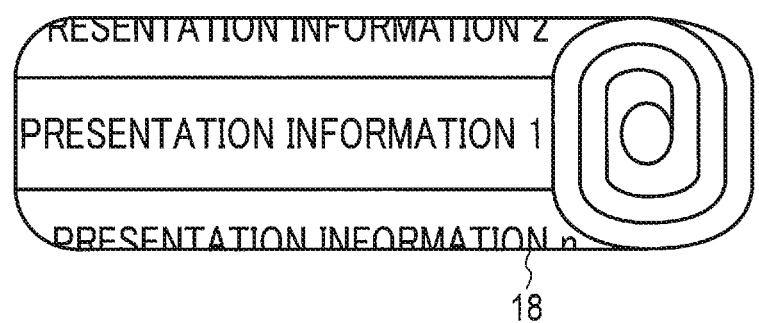
F I G. 3B

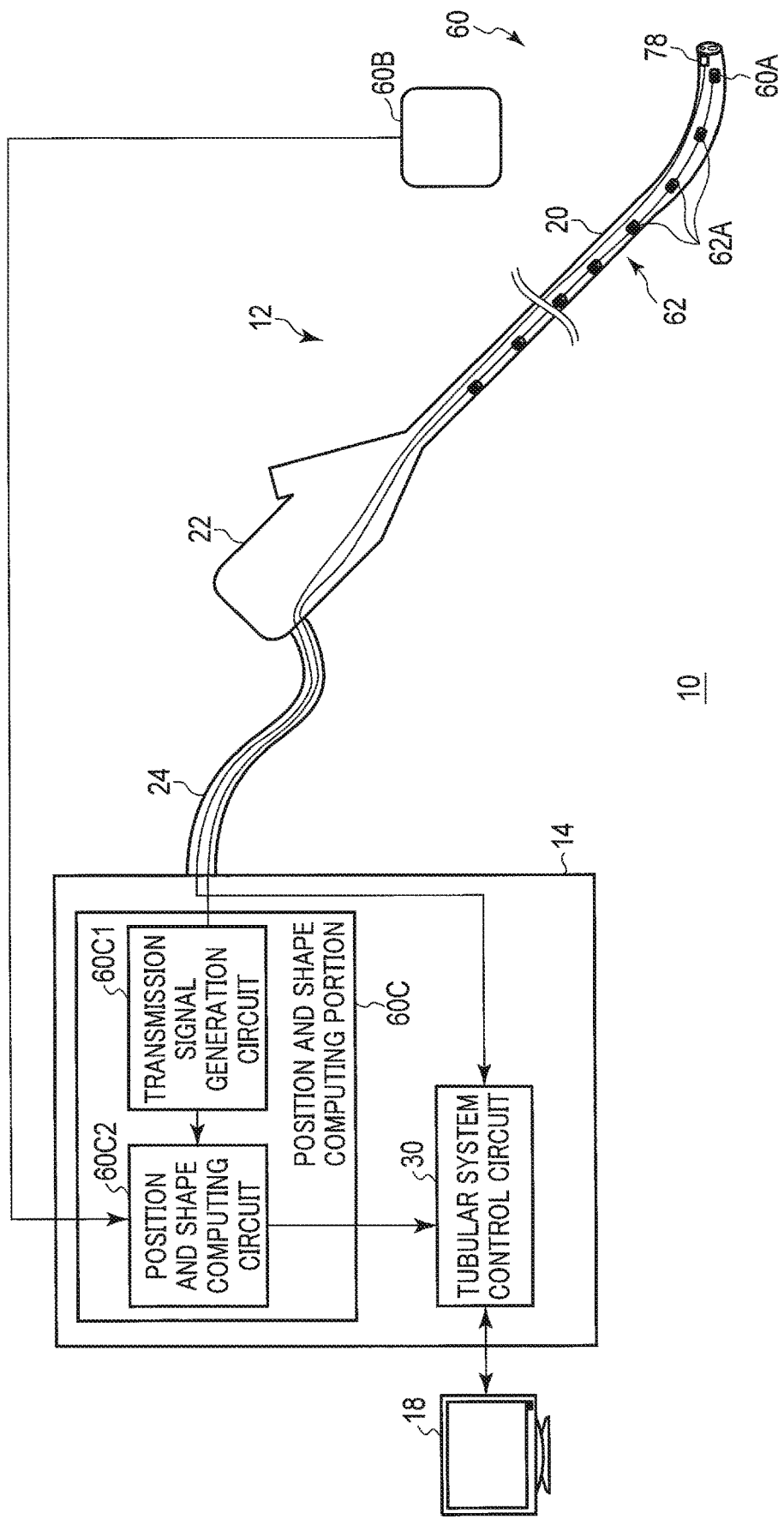
F I G. 5

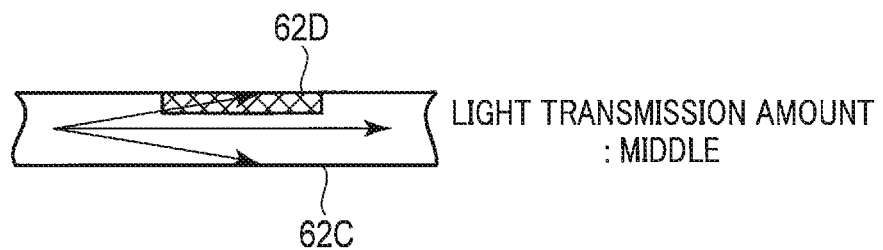
F I G. 7A
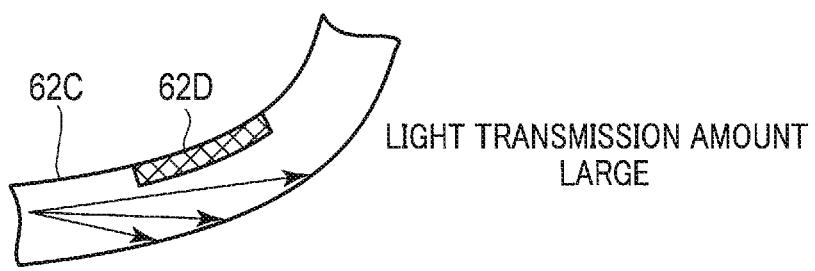
F I G. 7B
F I G. 7C

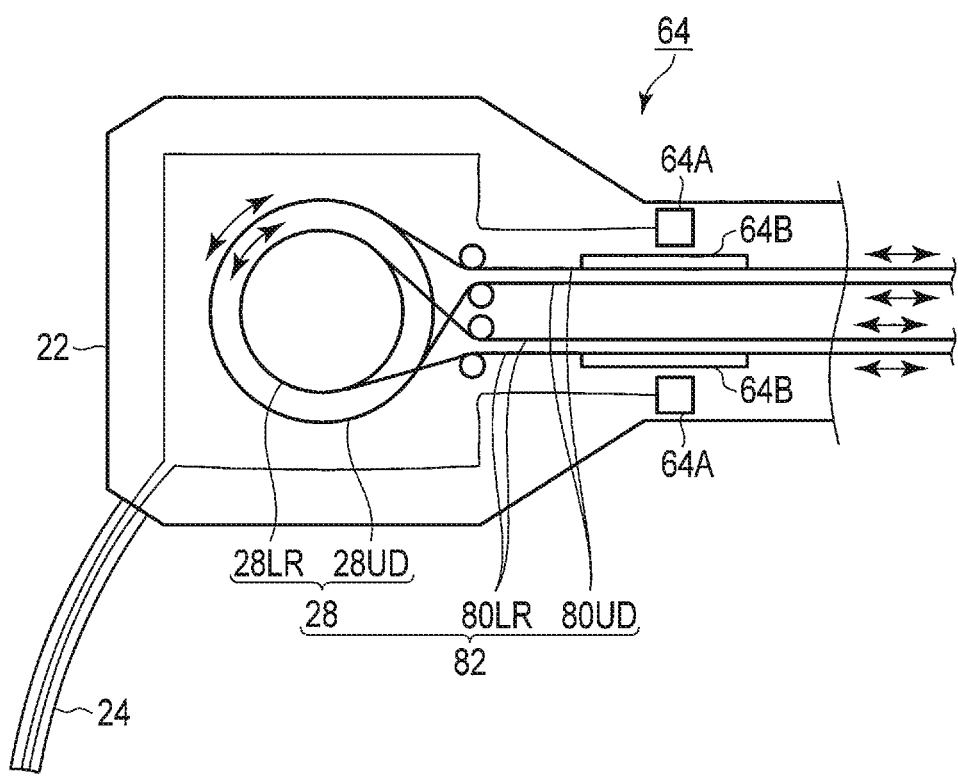
F I G. 8

| TIMING | INPUT INFORMATION EXAMPLE | STATE | PRESENTATION INFORMATION EXAMPLE |
|---|---|---|---|
| (1) BEFORE START OF INSERTION | TUBULAR SYSTEM FUNCTION SELECTION AND OPERATION CIRCUIT 52 | LIGHT SWITCH IS TURNED ON | - INSERTION START<br>- EXPLANATION OF HOSPITAL<br>- EXPLANATION OF OPERATOR<br>- EXPLANATION OF EXAMINATION<br>- RELAXING MUSIC<br>- ETC. |
| | OBSERVATION IMAGE BY IMAGE SENSOR 78 | INSERTION PORTION IS PRESENT OUTSIDE INSERTION SUBJECT AND HAS STARTED FROM STOPPED STATE | |
| | INSERTION SITUATION OBSERVATION SENSOR 68 | INSERTION SUBJECT GOES ON EXAMINATION TABLE, AND OPERATOR HOLDS INSERTION PORTION | |
| (2) WHEN INSERTING INSERTION PORTION INTO LUMINAL SPACE OF INSERTION SUBJECT | OBSERVATION IMAGE BY IMAGE SENSOR 78 | INSERTION PORTION IS INSERTED INTO INSERTION SUBJECT FROM OUTSIDE THEREOF | - INSERTION START<br>- EXPLANATION TO PROMOTE RELAXATION |
| | CURVED-SHAPE DETECTION SENSOR 62 DISTAL END POSITION DETECTION SENSOR 60 | INSERTION PORTION IS SET AT ENTRANCE OF LUMINAL SPACE OF INSERTION SUBJECT | |
| | INSERTION SITUATION OBSERVATION SENSOR 68 | INSERTION PORTION IS INSERTED INTO INSERTION SUBJECT | |
| (3) WHEN CORRECT INSERTION IS PERFORMED DURING INSERTION OF INSERTION PORTION | CURVED-SHAPE DETECTION SENSOR 62 OPERATION AMOUNT SENSOR 64 INSERTION SITUATION OBSERVATION SENSOR 68 (INSERTION SUBJECT POSTURE SENSOR 70, WEIGHT-DETECTION SENSOR 72 MAY BE POSSIBLE) | ARRANGEMENT AND SHAPE OF INSERTION PORTION IN INSERTION SUBJECT HAVE NORMAL SHAPE PATTERN, OR ARE IN PROPER CONDITION FOR INSERTION TIME THERE IS NO EXCESSIVE LOAD (FORCE) ONTO INSERTION SUBJECT | - EXPLANATION OF INSERTION SITUATION<br>- EXPLANATION TO PROMOTE RELAXATION |
| (4) WHEN INSERTION SUBJECT FEELS ANXIOUS | INSERTION SUBJECT STATE MONITORING MONITOR 74 | PULSE AND BREATHING STATE OF INSERTION SUBJECT ARE NORMAL BUT HAVE RISEN TO EXTENT OF FEELING ANXIOUS | - EXPLANATION TO PROMOTE RELAXATION |
| (5) WHEN INSERTION DIFFICULTIES OCCUR DURING INSERTION OF INSERTION PORTION | CURVED-SHAPE DETECTION SENSOR 62 OPERATION AMOUNT SENSOR 64 INSERTION SITUATION OBSERVATION SENSOR 68 (INSERTION SUBJECT POSTURE SENSOR 70, WEIGHT-DETECTION SENSOR 72 MAY BE POSSIBLE) | DETERMINED FROM ARRANGEMENT AND SHAPE OF INSERTION PORTION INSIDE INSERTION SUBJECT, MIDDLE OF INSERTION PORTION IS DEFLECTED AND PROPULSION (INSERTION) TO LUMINAL SPACE END OF DISTAL END IS INHIBITED | SIGN FOR REQUESTING POSTURAL CHANGE, ETC. |

FIG. 10A

| TIMING | INPUT INFORMATION EXAMPLE | STATE | PRESENTATION INFORMATION EXAMPLE |
|---|---|---|---|
| (6) WHEN INSERTION OF INSERTION PORTION IS COMPLETED (7) WHEN ENTERING EXAMINATION | CURVED-SHAPE DETECTION SENSOR 62 INSERTION SITUATION OBSERVATION SENSOR 68 OBSERVATION IMAGE BY IMAGE SENSOR 78 | ARRANGEMENT AND SHAPE OF INSERTION PORTION IN INSERTION SUBJECT, AND/OR OBSERVATION IMAGE, CONFIRM SMALL INTESTINAL ENTRANCE | - EXPLANATION OF EXAMINATION |
| (8) DURING EXAMINATION | CURVED-SHAPE DETECTION SENSOR 62 INSERTION SITUATION OBSERVATION SENSOR 68 OBSERVATION IMAGE BY IMAGE SENSOR 78 | AT TIME OF INVERTED VISUAL OBSERVATION SHAPE OF ANUS OF INSERTION PORTION IN INSERTION SUBJECT OR/AND WHEN INSERTION PORTION ITSELF CAN BE RECOGNIZED IN OBSERVATION IMAGE, ETC. | - EXPLANATION OF EXAMINATION STATUS |
| (9) WHEN POLYP OR AFFECTED SITE IS FOUND | OBSERVATION IMAGE BY IMAGE SENSOR 78 | POLYP SHAPE OR AFFECTED SITE IS DETERMINED | - EXPLANATION OF EXAMINATION STATUS OR TREATMENT STATUS |
| (10) (11) WHEN PERFORMING TREATMENT SUCH AS CLOSE EXAMINATION OR REMOVAL OF POLYP OR AFFECTED SITE | OBSERVATION IMAGE BY IMAGE SENSOR 78 | FORCEPS FOR BIOPSY IS CAPTURED IN OBSERVATION IMAGE | - EXPLANATION OF EXAMINATION STATUS OR TREATMENT STATUS |
| (12) WHEN INSERTION PORTION EMERGES FROM INSERTION SUBJECT | INSERTION SITUATION OBSERVATION SENSOR 68 OBSERVATION IMAGE BY IMAGE SENSOR 78 | INSERTION PORTION EMERGES FROM INSERTION SUBJECT | - EXPLANATION AFTER COMPLETION |
| (13) WHEN INSERTION OF INSERTION PORTION IS FINISHED | TUBULAR SYSTEM FUNCTION SELECTION AND OPERATION CIRCUIT 52 | LIGHT SWITCH IS TURNED OFF | — |
| | OBSERVATION IMAGE BY IMAGE SENSOR 78 | INSERTION PORTION IS PRESENT OUTSIDE INSERTION SUBJECT AND IS IN STOPPED STATE | |
| | INSERTION SITUATION OBSERVATION SENSOR 68 | OPERATOR RELEASES INSERTION PORTION, AND INSERTION SUBJECT IS LOWERED FROM EXAMINATION TABLE | |

FIG. 10B

| ◆SELECTION OF PRESENTATION INFORMATION | | |
|---|---|---|
| | PRESENTATION | |
| PRESENTATION INFORMATION 1 | ON | OFF |
| PRESENTATION INFORMATION 2 | ON | OFF |
| PRESENTATION INFORMATION 3 | ON | OFF |
| PRESENTATION INFORMATION 4 | ON | OFF |
| ⋮ | | |
| PRESENTATION INFORMATION n | ON | OFF |

| ◆SELECTION OF PRESENTATION METHOD | | |
|---|---|---|
| PRESENTATION LANGUAGE | JAPANESE | |
| VOICE | ON | OFF |
| DISPLAY | ON | OFF |
| PRESENTATION LANGUAGE | ENGLISH | |
| VOICE | ON | OFF |
| DISPLAY | ON | OFF |
| ⋮ | | |

F I G. 12

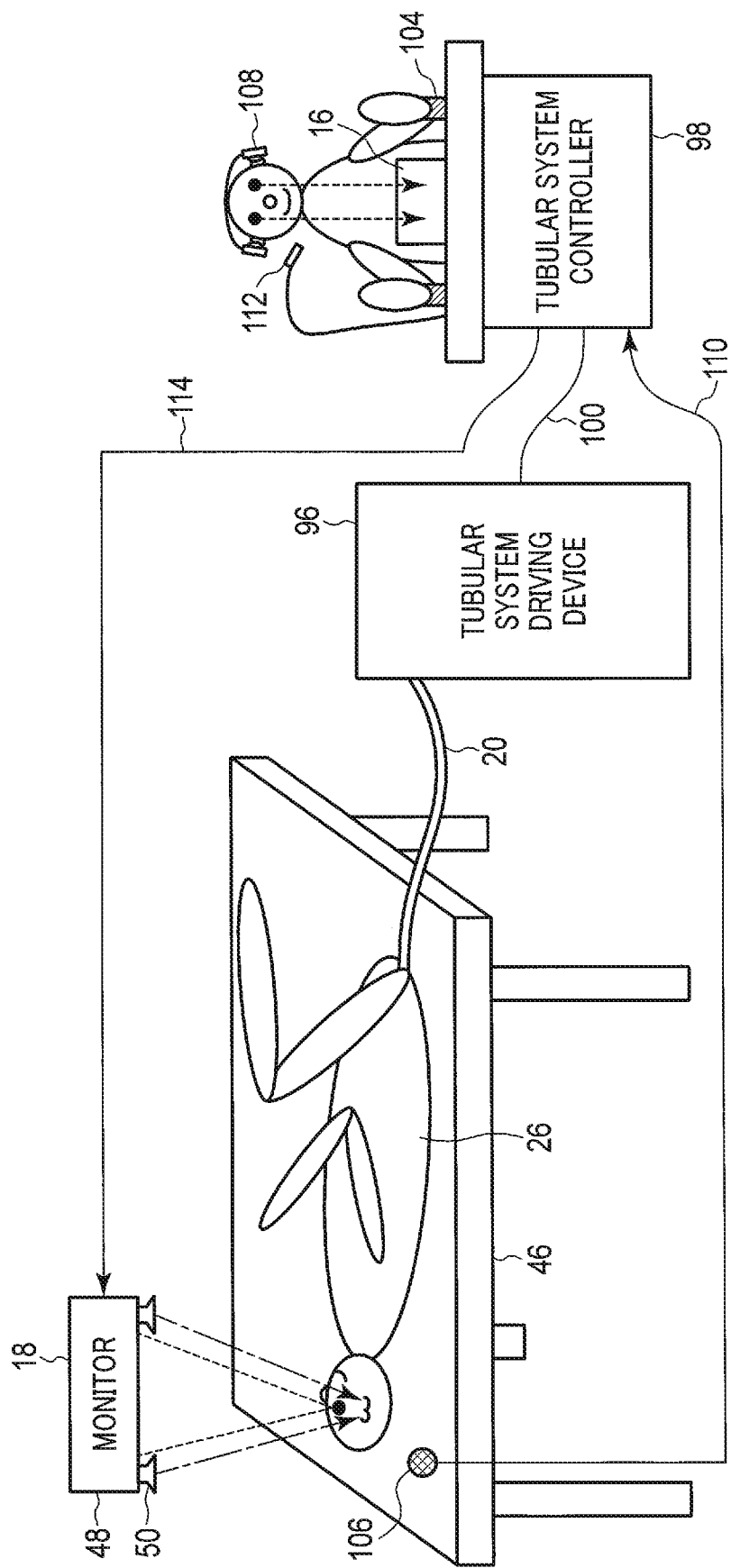
F I G. 14

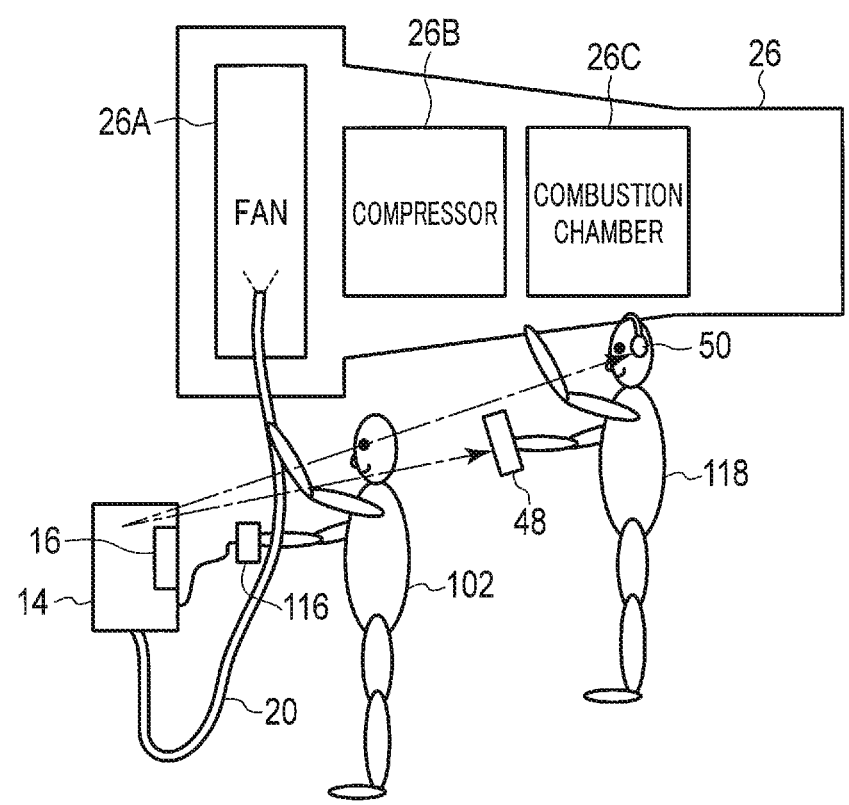
F I G. 15

INFORMATION PRESENTATION SYSTEM INCLUDING A FLEXIBLE TUBULAR INSERTION PORTION

CROSS-REFERENCE TO RELATED APPLICATIONS

This application is a Continuation Application of PCT Application No. PCT/JP2016/085200, filed Nov. 28, 2016, the entire contents of which are incorporated herein by reference.

FIELD

The embodiments of present disclosure relate to an information presentation system mounted on a tubular system provided with a flexible tubular insertion portion to be inserted into a subject, and presenting information to a non-operator.

BACKGROUND

There are previous endoscope systems that provide not only sensor information but also useful support information for an operator in the form of information related to an insertion portion. The support information is typically generated by using the following first to fourth pieces of information.

First information: information indicating at least one of an insertion state and an operation state in a body cavity of an insertion portion that performs a predetermined operation, Second information: operation support information of the subject insertion system, Third information: information related to the subject, and Fourth information: information related to operations.

SUMMARY

An information presentation system including a tubular system including a flexible tubular insertion portion configured to be inserted into an insertion subject, a storage medium configured to store a plurality of pieces of presentation information recognizable by a non-operator, a non-operator presentation display configured to present information in an output form recognizable by the non-operator and a processor including hardware, the processor configured to perform a selection of presentation information to be presented to the non-operator presentation display, and switch a presentation period of the selected presentation information to the non-operator presentation display.

Advantages of the disclosed embodiments will beset forth in the description which follows. The advantages of the disclosed embodiments may be realized and obtained by means of the instrumentalities and combinations particularly pointed out hereinafter.

BRIEF DESCRIPTION OF THE DRAWINGS

The accompanying drawings, which are incorporated in and constitute apart of the specification, illustrate embodiments of the disclosure, and together with the general description given above and the detailed description of the embodiments given below, serve to explain the principles of the disclosure.

FIG. 1 is a schematic diagram showing a configuration of an endoscope system as an information presentation system according to a first embodiment of the present disclosure.

FIG. 2 is a diagram showing presentation information and a specific example thereof.

FIG. 3A is a diagram showing another example of a presentation display for a non-operator.

FIG. 3B is a diagram showing a further example of the non-operator presentation display.

FIG. 5 is a diagram showing a configuration example of a magnetic position sensor as a distal end position detection sensor and a curved-shape detection sensor.

FIG. 7A is a diagram for explaining a detection principle of the fiber-shape sensor of FIG. 6.

FIG. 7B is a diagram for explaining the detection principle of the fiber-shape sensor of FIG. 6.

FIG. 7C is a diagram for explaining the detection principle of the fiber-shape sensor of FIG. 6.

FIG. 8 is a diagram showing a configuration example of an operation amount sensor.

FIG. 10A is a diagram showing an example of a state of a tubular system and/or an insertion subject detected by a state detection circuit, and selection of presentation information by a presentation information generation circuit.

FIG. 10B is a diagram showing an example of a state of the tubular system and/or the insertion subject detected by the state detection circuit, and selection of presentation information by the presentation information generation circuit.

FIG. 12 is a diagram showing an example of a selection screen of presentation information and a presentation method.

FIG. 14 is a diagram showing an example of a use scene of the information presentation system.

FIG. 15 is a diagram showing another example of a use scene of the information presentation system.

DETAILED DESCRIPTION

Figure 4:
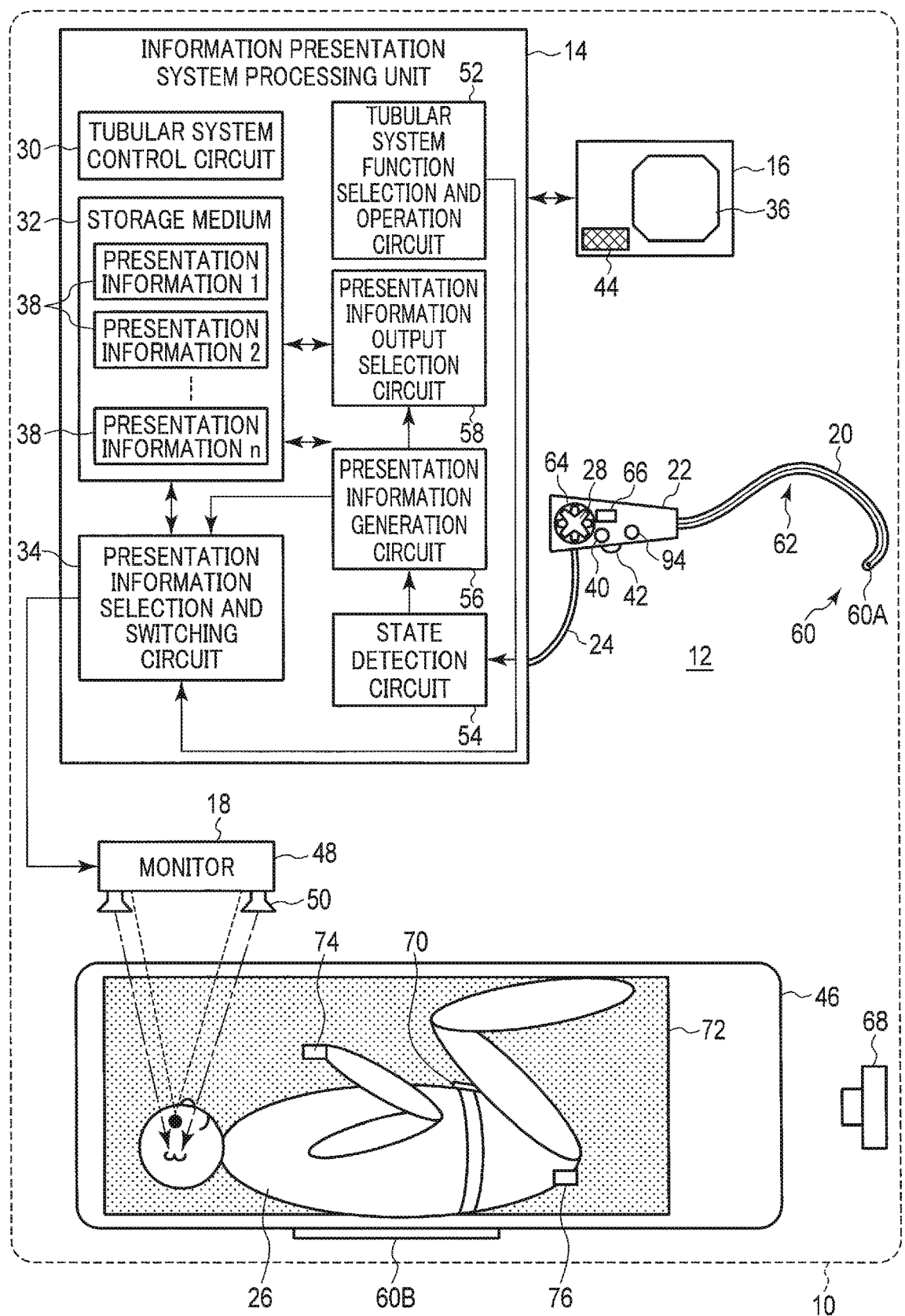
FIG. 4 is a schematic diagram showing a configuration of an endoscope system as an information presentation system according to a second embodiment of the present disclosure.

Hereinafter, embodiments for carrying out the present disclosure will be described with reference to the drawings.

First Embodiment

As shown in FIG. 1, an information presentation system 10 according to a first embodiment of the present disclosure includes a tubular system 12, an information presentation system processing unit 14 (which can be a portion of a processor and/or a CPU), a display 16 for an operator, and a presentation display 18 for a non-operator.

The tubular system 12 comprises an elongated insertion portion 20 which is a bending member, an operation portion 22 coupled to a proximal end of the insertion portion 20, and a connection cable 24 that connects the operation portion 22 and the information presentation system processing unit 14. The tubular system 12 is a tubular insertion device that inserts the tubular insertion portion 20 into an insertion subject 26, which is a human in this embodiment, more specifically a large intestine lumen, and performs observation and/or treatment of an internal portion of the insertion subject 26.

In this embodiment, as the tubular system 12, an endoscope specifically, a flexible endoscope for the large intestine is described by way of example, but any tubular system may be used as long as it is a tubular system including an insertion portion, at least a part of which has flexibility and which can be inserted into the insertion subject 26. Also, the insertion subject 26 is not limited to a human body, and may be an animal or other structure. For example, the tubular system 12 may be a catheter, other than an endoscope (an upper gastrointestinal endoscope, a large intestine endoscope, an ultrasonic endoscope, a cystoscope, a pyeloscope, a bronchoscope, etc.). Moreover, it may be a manipulator, an industrial endoscope, a treatment tool, etc.

The insertion portion 20 includes a distal end hard section, an operation bending section that bends, and a flexible tube section, from a distal end side to a proximal end side of the insertion portion 20. Here, the distal end hard section is a distal end of the insertion portion 20 and a distal end of the tubular system 12, and is a substantially hard, substantially inflexible member. An image sensor (e.g., a CCD, etc.), which is an imaging unit, is built in the distal end hard section. The operation bending section can be bent in a desired direction by an operator such as a doctor operating an operation knob 28 provided in the operation portion 22. The flexible tube section has a configured flexibility, and bends by an external force. The operator can insert the insertion portion 20 from an entrance of the insertion subject 26, which is an anus in this embodiment, and observes the inside of the large intestine lumen with the image sensor provided at the distal end.

The information presentation system processing unit 14 includes a tubular system control circuit 30, a storage medium (memory) 32, and a presentation information selection and switching circuit 34.

The tubular system control circuit 30 performs a series of controls, to control a light source device (not shown) to supply illumination to the distal end of the insertion portion 20, perform image processing on an image captured by the image sensor, and display a result thereof as an observation image 36 on the operator display 16. This tubular system control circuit 30 is configured by a hardware circuit. Alternatively, a software program for causing a computer processor to function as this tubular system control circuit 30 may be prepared in a memory (not shown), and the processor may execute the program so that the function of the tubular system control circuit 30 may be performed by the processor. The tubular system control circuit 30 may be configured separately from the information presentation system processing unit 14. In that case, the information presentation system processing unit 14 can be similarly mounted on a trolley on which the tubular system control circuit 30 is mounted.

The storage medium 32 is, for example, a semiconductor memory in which a plurality of presentation information 38, which can be recognized (understood) by a non-operator who is not the operator of the insertion portion 20, are stored in advance.

Here, the operator does not mean only a doctor who performs an insertion operation of the insertion portion 20 by operating the insertion portion 20 and the operation portion 22 of the tubular system 12, etc. The operator also includes a nurse (or other medical practitioner) who operates the information presentation system processing unit 14, the operator display 16, and the non-operator presentation display 18, and holds down and moves a human as the insertion subject 26 to assist in the insertion operation of the insertion portion 20. As described above, in the present embodiment, the operator includes a main operator who performs the insertion operation of the insertion portion 20, such as a doctor (or other medical practitioner), and an auxiliary operator who assists in the insertion operation by the main operator, such as a nurse (or other medical practitioner).

On the other hand, the non-operator is not limited to the insertion subject 26. For example, if the insertion subject 26 is an animal that cannot understand the presentation information, it includes an owner who can control a movement and/or an emotion of the animal to some extent. When the insertion subject 26 is a machine as in an industrial endoscope, it includes a controller who controls the machine, a robot having a cognitive ability, etc.

Thus, the presentation information 38 is information to be provided to a non-operator who is not the operator of the tubular system 12, a group on the insertion subject 26 side, who can recognize (understand) the presentation information 38. A purpose of this presentation information 38 includes being able to help the non-operator recognize a sign to perform a predetermined action to support insertion by said operator, and enabling the non-operator to know the situation of the insertion.

As this presentation information 38, for example, as shown in FIG. 2, an insertion start message, an explanation of a hospital message, an explanation of an operator message, an explanation of an examination message, an explanation of an insertion situation message, a sign message, an explanation to promote relaxation message, an explanation of an examination status or a treatment status message, an explanation after completion message, and others.

The presentation information selection and switching circuit 34 performs selection of the presentation information 38, to be presented to the non-operator presentation display 18, from among a plurality of pieces of presentation information 38 stored in the storage medium 32 and switching of a presentation period of the selected presentation information 38, according to an operation of a selection and switching operation member by the operator.

Here, the selection and switching operation member includes a dedicated electrical switch, a release switch, a keyboard, a foot switch, an eye-gaze input, etc. The dedicated electrical switch includes, for example, a selection button 40 and a switching dial 42, respectively provided in the operation portion 22 of the tubular system 12.

The presentation information selection and switching circuit 34 causes the operator display 16 to display a presentation information content selection display 44 at a position near the observation image 36, so that the operator can confirm from the observation image 36 with comparatively less eye movement. The presentation information content selection display 44 is, for example, a display representing the content of one of the plurality of pieces of presentation information 38 stored in the storage medium 32. The presentation information selection and switching circuit 34 switches the presentation information 38 to be displayed according to an operation of the switching dial 42 by the operator, and when the selection button 40 is operated by the operator, presents the presentation information 38 displayed as the presentation information content selection display 44, at that time, to the non-operator through the non-operator presentation display 18. That is, the operator, by observing a situation of the examination and a situation of the insertion subject 26, selects the presentation information 38 to be presented, and presents it to the non-operator. Information to be presented can be switched by selecting presentation information 38 that is different from the one currently presented. That is, a presentation period is switched by a selection operation of the presentation information 38.

The presentation information selection and switching circuit 34 is configured by a hardware circuit. Alternatively, a software program for causing a computer processor to function as the presentation information selection and switching circuit 34 may be prepared in a memory (not shown), and the processor may execute the program, so that the function of the presentation information selection and switching circuit 34 may be performed by the processor.

In addition, it is also possible for a nurse, etc. who is an auxiliary operator to select the presentation information 38 to be presented, by another selection and switching operation member (not shown), and present it to the non-operator.

The non-operator presentation display 18 can include, for example, a monitor 48 and a speaker 50 arranged so as to be viewable by a human as the insertion subject 26 lying on an examination table 46. In addition, instead of the monitor 48, it is possible to use an indicator light which light-displays information selected from the display showing the content of the plurality of pieces of presentation information 38 as shown in FIG. 3A or a rotary direction curtain on which the content of the selected presentation information 38 is presented at a presentation position by a sheet on which the contents of the plurality of pieces of presentation information 38 are described being wound/rolled up, as shown in FIG. 3B. Furthermore, for a visually-impaired person, a tactile (e.g. Braille) display, etc. may be used, instead of the monitor 48.

When the tubular system 12 is an industrial endoscope, etc., a non-operator, such as a controller, may be located at a remote position with respect to the insertion subject 26. In that case, the non-operator presentation display 18 is arranged at a place viewable by the non-operator. Alternatively, in a case where the non-operator is a robot, etc. having a cognitive ability, the non-operator display 18 may include an input device provided in the robot, etc. That is, the robot can recognize the contents of the presentation information 38 inputted by the input device as the non-operator presentation display 18, and change the state of the insertion subject 26 to a state suitable for the insertion of the insertion portion 20.

An operator, such as a doctor, can operate the tubular system 12 (here, a flexible endoscope for the large intestine) to insert the insertion portion 20 into the large intestine of a patient, who is the insertion subject 26 lying on the examination table 46. In this case, the operator performs insertion of the insertion portion 20 through the rectum, the sigmoid colon, the descending colon, the transverse colon, and the ascending colon, and performs the insertion operation up to the cecum (which is an entrance of the small intestine). Thus, when the insertion of the insertion portion 20 to the cecum is completed, the operator examines the entire large intestine for the presence or absence of abnormalities while removing the insertion portion 20. In the middle of the examination, an area suspected of being an affected site can be subjected to treatment, such as a "biopsy" or "ablation" of a tissue. For large tumors, etc., an insertion operation for the purpose of treatment can also be performed.

In such a situation, in the information presentation system 10 according to the present embodiment, the operator selects the presentation information 38 to be presented by observing the situation of the examination and the situation of the insertion subject 26; and the content of the selected presentation information 38 is provided to the patient as video or text information on the monitor 48, etc. as the non-operator presentation display 18, or as audio information from the speaker 50.

The selection of the presentation information 38 by the operator is performed by rotating the switching dial 42 to obtain a target content for the presentation information content selection display 44, displayed on the operator display 16 by the presentation information selection and switching circuit 34, and inputting a decision with the selection button 40. Although not shown, selection and determination can be substituted by members having equivalent functions, such as a foot switch, a keyboard, an eye-gaze input, etc.

As described above, the information presentation system 10 according to the present embodiment comprises the tubular system 12 (that performs observation and treatment of an internal portion of the insertion subject 26), including the flexible tubular insertion portion 20 to be inserted into the insertion subject 26 by an insertion operation of an operator; the storage medium 32 that stores in advance a plurality of pieces of presentation information 38 which can be recognized (understood) by a non-operator who is not the operator; the non-operator presentation display 18 that presents information in an output form that can be recognized (understood) by the non-operator; and the presentation information selection and switching circuit 34 that performs selection of the presentation information 38 to be presented to the non-operator presentation display 18 and switching of a presentation period of the selected presentation information 38.

Accordingly, it is possible to provide the information presentation system 10 capable of storing a plurality of pieces of presentation information 38 related to insertions, recognizable by the non-operator, in advance, and presenting at least one of them appropriately to the non-operator to enable relatively easier insertion of the insertion portion 20 into the insertion subject 26.

In particular, when the operator operating the tubular system 12 instructs the insertion subject 26 about a postural change, respiration, etc. to facilitate insertion, examination, treatment, etc., it is possible to convey a sign to the insertion subject 26, instructing said subject to perform a desired predetermined action, without direct communication between the operator and the non-operator. Therefore, the operator can concentrate on insertion, examination and/or treatment.

In addition, even in the case of the insertion subject 26 being unable to understand the operator's language, such as when the language used is different from the operator's language, or even if the insertion subject 26 cannot respond to a specific communication method (talking and instructing, etc.), perhaps through being deaf, a message can still be transmitted. The operator can concentrate on insertion, examination, and treatment, thereby enabling a relatively easy operation, examination, and/or treatment.

Furthermore, for the insertion subject 26, it is possible to understand the track records of the hospital and the operator, and the meaning of the examination and treatment. This embodiment can therefore gain knowledge of the state of implementation of the insertion operation, examination, and treatment in real time. As a result, it is possible to prevent and/or reduce a situation in which the insertion of the insertion portion 20 is inhibited, by, for example, hardening due to tension of the insertion subject 26. Thereby, the insertion of the insertion portion 20 is facilitated, and the insertion operation, examination, and/or treatment can be performed. At the same time, it is possible to shorten the time taken for the insertion operation, examination and treatment (a load on the insertion subject 26 is also reduced).

Second Embodiment

Next, a second embodiment of the present disclosure will be described. Hereinafter, the same structural members as those in the first embodiment are assigned with the same reference numerals, and descriptions thereof are omitted while describing only parts different from the first embodiment.

As shown in FIG. 4, an information presentation system 10 according to the second embodiment of the present disclosure includes at least one detection device in addition to the configuration of the above-described first embodiment. In addition to the configuration of the above-described first embodiment, the information presentation system processing unit 14 comprises a tubular system function selection and operation circuit 52, a state detection circuit 54, a presentation information generation circuit 56 and a presentation information output selection circuit 58.

Here, the tubular system function selection and operation circuit 52 inputs information required to control the tubular system 12. The state detection circuit 54 detects a state of the tubular system 12 and/or the insertion subject 26, based on an output of the detection device. The presentation information generation circuit 56 generates, based on at least one or more states detected by the state detection circuit 54, a specification information which specifies selection and a presentation time of the presentation information 38 to be presented to the non-operator display 18. The presentation information selection and switching circuit 34 performs the selection of the presentation information 38, and switching of a presentation period, in accordance with the specification information generated by this presentation information generation circuit 56.

In addition, the presentation information output selection circuit 58 selects the presentation information 38 and a presentation method (a language, an output destination (the monitor 48, the speaker 50, etc.)) to be presented to the non-operator. When the selection by the presentation information output selection circuit 58 is performed, in accordance with the selection, the presentation information generation circuit 56 generates specification information which specifies the selection and presentation period of the presentation information 38 and the presentation method to the non-operator presentation display 18. Then, the presentation information selection and switching circuit 34 switches the selection and the presentation period of the presentation information 38 and the presentation method to the non-operator presentation display 18, in accordance with the specification information generated by the presentation information generation circuit 56.

The tubular system function selection and operation circuit 52, the state detection circuit 54, the presentation information generation circuit 56, and the presentation information output selection circuit 58 each are configured by a hardware circuit. Alternatively, a software program for causing the computer processor to function as at least one of: the tubular system function selection and operation circuit 52, the state detection circuit 54, the presentation information generation circuit 56, and the presentation information output selection circuit 58 may be prepared in a memory (not shown), and the processor may execute the program so that the at least one of the functions may be performed by the processor.

The detection devices include, for example, a distal end position detection sensor 60, a curved-shape detection sensor 62, an operation amount sensor 64, a posture sensor 66, an insertion situation observation sensor 68, an insertion subject posture sensor 70, a weight-detection sensor 72, an insertion subject state monitoring monitor 74, and an insertion amount detection sensor 76 (without providing a dedicated sensor, an insertion amount can be calculated by a distal end position detection sensor which stores a position of the anus at the start of an anal insertion to determine a positional relationship with the curved-shape detection sensor 62 (magnetic type) arranged in the tubular system), etc. In addition, the above-described switching dial 42 and the above-described tubular system function selection and operation circuit 52 can also be used as the detection devices. Alternatively, the image sensor arranged at the distal end of the insertion portion 20 can be used. As a matter of course, other detection devices than the above may be used, such as a microphone for detecting a voice given by the insertion subject 26. Thus, among the components of the information presentation system processing unit 14, in particular, the state detection circuit 54 can be configured by a computer processor that executes a preset operation processing program or algorithm, rather than being implemented by a hardware circuit, so as to be able to cope with various types of detection processing.

Here, the distal end position detection sensor 60 is a sensor used to detect the distal end position of the insertion portion 20, and the curved-shape detection sensor 62 is a sensor used to detect the curved shape and the degree of bending of the insertion portion 20. These distal end position detection sensor 60 and curved-shape detection sensor 62 can be configured by, for example, a magnetic position sensor as disclosed in International Publication No. WO 94/04938, the entire contents of which are incorporated by reference.

That is, the distal end position detection sensor 60 arranges one magnetic coil at the distal end of the insertion portion 20, and detects its position with reference to a magnetic sensor antenna, thereby detecting distal end position information of the insertion portion 20. In addition, the curved-shape detection sensor 62 can include a plurality of magnetic coils in the insertion portion 20 along its longitudinal direction, can detect at least positions (directions may be used) of these magnetic coils with reference to the magnetic sensor antenna, and can interpolate and connect detection positions of the plurality of magnetic coils, thereby detecting the curved shape of the insertion portion 20.

Specifically, as shown in FIG. 5, a plurality of transmission coils, which are a part of the magnetic position detection sensor, are arranged in the insertion portion 20. Among the plurality of transmission coils, one transmission coil 60A, arranged at the distal end of the insertion portion 20, is a magnetic coil of the distal end position detection sensor 60. A plurality of transmission coils 62A, arranged at different positions in the longitudinal direction of the insertion portion 20, are magnetic coils of the curved-shape detection sensor 62. These transmission coils 60A and 62A generate magnetic field signals when a current (to be described later) flows from the information presentation system processing unit 14.

The magnetic field signals that can be generated by these transmission coils 60A and 62A are detected by a receiving antenna 60B which is a part of the magnetic position detection sensor. Although not shown, the receiving antenna 60B is composed of a plurality of receiving coils, and detects the magnetic field signals generated by the transmission coils 60A and 62A. Accordingly, the receiving antenna 60B is a magnetic sensor antenna of the distal end position detection sensor 60, and also functions as a magnetic sensor antenna of the curved-shape detection sensor 62. Intensity information of the magnetic field detected by the receiving antenna 60B is inputted to a position and shape computing portion 60C provided in the information presentation system processing unit 14. The position and shape of computing portion 60C is a part of the magnetic position detection sensor. Since this position and shape computing portion 60C calculates the positions of the transmission coils 60A and 62A based on the intensity of the detected magnetic field, the receiving antenna 60B is fixed in position in the vicinity of the insertion subject 26, and fixed so as not to move with respect to the examination table 46, such as a room or a bed.

On the other hand, the position and shape computing portion 60C includes a transmission signal generation circuit 60C1 and a position and shape computing circuit 60C2. These transmission signal generation circuit 60C1 and position and shape computing circuit 60C2 may be configured by individual hardware circuits, or some may be configured together as one hardware circuit. Also, a software program for causing a computer processor to function as the transmission signal generation circuit 60C1 and/or the position and shape computing circuit 60C2 may be prepared in a memory (not shown), and the processor may execute the program so that the processor may perform at least one function of these units.

This transmission signal generation circuit 60C1 generates a signal for generating a magnetic field from the transmission coils 60A and 62A of the insertion portion 20, e.g., a sinusoidal current. The generated signal is output in the order determined for each of the plurality of transmission coils 60A and 62A, e.g., from the transmission coils 60A and 62A on the distal end side of the insertion portion 20. Although only one wire is shown in FIG. 5 for simplification of the drawing, two wires per transmission coil 60A, 62A are inserted from this transmission signal generation circuit 60C1 through the connection cable 24, the operation portion 22, and the insertion portion 20. In addition, the transmission signal generation circuit 60C1 supplies output timing information indicating to which transmission coil 60A, 62A a signal is output at this moment, to the position and shape computing circuit 60C2.

The position and shape computing circuit 60C2 is connected to the transmission signal generation circuit 60C1 and the receiving antenna 60B. The position and shape computing circuit 60C2 calculates the position information of each transmission coil 60A, 62A based on the intensity information of the magnetic field input from the receiving antenna 60B and the output timing information supplied from the transmission signal generation circuit 60C1. Then, the position and shape computing circuit 60C2 acquires the obtained position information of the plurality of transmission coils 60A and 62A as the distal end position information of the insertion portion 20 and shape information of the insertion portion 20. In addition, the position and shape computing circuit 60C2 may interpolate the position information of these plurality of transmission coils 60A and 62A by, for example, spline processing, etc. to acquire a result thereof as the shape information. As described above, the position information and/or the shape information indicates a state of a portion where the transmission coils 60A and 62A of the insertion portion 20 are arranged, i.e., at least a part of the insertion portion 20. Hereinafter, the position information and/or the shape information are referred to as "state information". The position and shape computing circuit 60C2 outputs the state information thus obtained to the tubular system control circuit 30.

The tubular system control circuit 30 performs image processing for displaying and outputting the state information of the insertion portion 20, input from the position and shape computing circuit 60C2 of the position and shape computing portion 60C, on the operator display 16. Furthermore, the tubular system control circuit 30, for example, receives an image signal from an image sensor 78 that images the large intestine lumen, performs general image processing on the image signal, and generates the observation image 36. Then, the tubular system control circuit 30 generates a display image including these state information and observation image 36, and outputs the display image to the operator display 16.

The operator display 16 is, for example, a liquid crystal display in which an input unit, such as a touch panel, is disposed on a display screen. The operator display 16 displays the observation image 36 and displays the state information, and the operator be able to observe the large intestine lumen and know the state of the insertion portion 20 by looking at a display screen of the operator display 16. In addition, various setting screens of the tubular system 12 are displayed on the operator display 16 so that various settings can be performed by a touch panel operation. In other embodiments, instead of attaching a touch panel to the operator display 16, a dedicated input device may be provided separately.

Also, for the curved-shape detection sensor 62, a fiber-shape sensor can be used, or a plurality of strain sensors can be used in combination.

Figure 6:
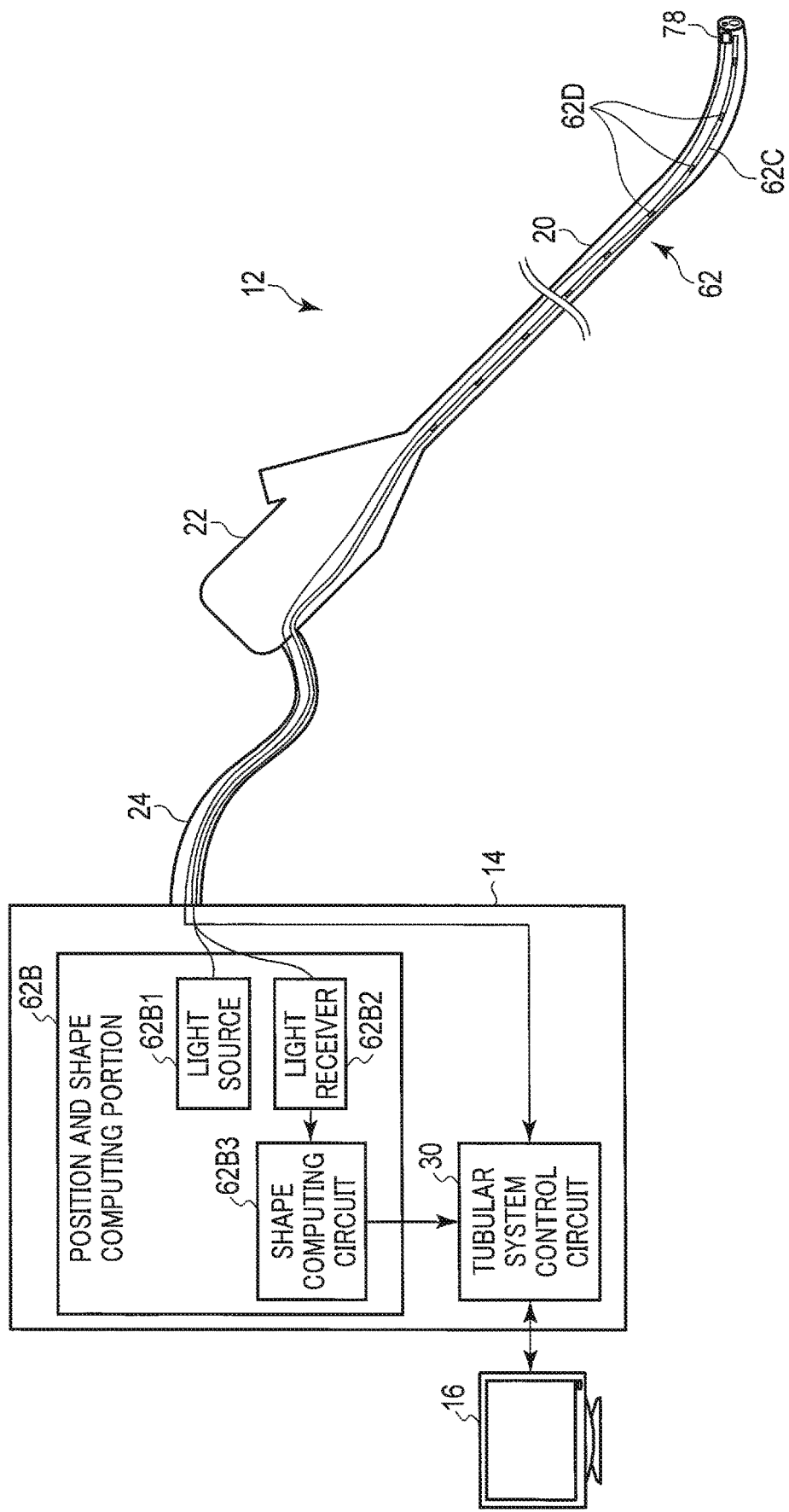
FIG. 6 is a diagram showing a configuration example of a fiber-shape sensor as a curved-shape detection sensor.

Fiber-shape sensors are disclosed in, for example, International Publication No. WO 2015/146712, International Publication No. WO 2015/198773, etc. the contents of both of which are incorporated in their entirety by reference. When a fiber-shape sensor is used as the curved-shape detection sensor 62, as shown in FIG. 6, the information presentation system processing unit 14 comprises a position and shape-computing portion 62B including a light source 62B1, a light-receiving portion 62B2, such as a light-receiving element, and a shape-computing circuit 62B3. In addition, the insertion portion 20 is provided with an optical fiber 62C including a plurality of detection subject portions 62D. In this case, the detection subject portion 62D is arranged at a portion where the shape detection of the insertion portion 20 is to be performed. Light emitted from the light source 62B1 is incident on the optical fiber 62C, and is guided in the optical fiber 62C. A return light reflected by a reflector (not shown) provided at a distal end of the optical fiber 62C and guided in the optical fiber 62C again is detected by a light receiver 62B2.

When the insertion portion 20 is bent, the optical fiber 62C, provided along the longitudinal direction of the insertion portion 20, also bends in accordance with the bending of the insertion portion 20. Thus, when the optical fiber 62C is bent, the detection subject portion 62D provided in the optical fiber 62C emits (leaks) apart of the light transmitted in the optical fiber 62C toward the outside of the optical fiber 62C, according to the bending state of the optical fiber 62C, or absorbs the same. That is, the detection subject portion 62D is provided on one side surface of the optical fiber 62C, and emits a part of the light to be transmitted to the outside, or absorbs the same, according to the bending of the optical fiber 62C. The amount of light emitted by the detection subject portion 62D toward the outside of the optical fiber 62C, or absorbed by the detection subject portion 62D, corresponds to a bending amount of the optical fiber 62C. That is, the detection subject portion 62D is processed to leak the light of a light amount corresponding to the bending amount of the optical fiber 62C to the outside of the optical fiber 62C, or to absorb the same. In other words, the detection subject portion 62D serves to change optical characteristics of the light guided by the optical fiber 62C, e.g., a light amount, according to the bending state of the insertion portion 20.

FIGS. 7A, 7B, and 7C are schematic views of a light transmission amount according to the bending of the optical fiber 62C. FIG. 7A shows a light transmission amount when the optical fiber 62C is not bent. FIG. 7B shows a light transmission amount when the optical fiber 62C is bent to the side provided with the detection subject portion 62D. FIG. 7C shows a light transmission amount when the optical fiber 62C is bent to an opposite side to the side provided with the detection subject portion 62D. As shown in FIGS. 7A to 7C, the light transmission amount when the optical fiber 62C is bent to the side provided with the detection subject portion 62D is the largest, the light transmission amount when the optical fiber 62C is not bent is the next largest, and the light transmission amount when the optical fiber 62C is bent to the opposite side to the side provided with the detection subject portion 62D is the smallest.

Supply of light to the optical fiber 62C arranged in the insertion portion 20, and detection of light from the optical fiber 62C, are performed by connecting the optical fiber 62C from the insertion portion 20 through the operation portion 22 and the connection cable 24 to the position and shape-computing portion 62B. For example, the supply of light is performed by passing light emitted from the light source 62B1 for the fiber-shape sensor through a light distributor, such as a half mirror or a beam splitter, collecting the light with a light-collecting lens in a light incident and emitting portion, and making the light incident on the optical fiber 62C. Detection of the light is performed in the light receiver 62B2 by receiving the light emitted from the optical fiber 62C at the above light incident portion and making the light into parallel light, and reflecting the parallel light by, for example, 90 degrees by the above the light distributor to be incident on the light receiver 62B2. The light receiver 62B2 receives the light incident from the optical fiber 62C, and outputs a light reception signal according to an amount of light received, etc. That is, the light receiver 62B2 outputs a light-receiving signal according to the magnitude (the bending amount) of bend of the insertion portion 20 based on the incident light.

A shape computing circuit 62B3 computes the shape of the insertion portion 20 from the bending amount of the insertion portion 20 at a position of each of the detection subject portions 62D, indicated by the light reception signal from the light receiver 62B2, to obtain shape information. This shape information is output to the tubular system control circuit 30 as state information. This shape-computing circuit 62B3 is configured by a hardware circuit. Alternatively, a software program for causing a computer processor to function as this shape-computing circuit 62B3 may be prepared in a memory (not shown) and the processor may execute the program, so that the processor may perform the function of the shape-computing circuit 62B3.

In addition, in the light source 62B1, a laser diode (LD), an LED, a lamp, or light obtained by causing a fluorescent material to emit light via these lights can be used. By combining a plurality of them, light having wavelength characteristics required for a fiber-shape sensor (e.g., white light) can be adjusted. The light source 62B1 referred to here also includes a lens system in which, if a light distributor is a fiber coupler, light is collected and incident on a fiber of a fiber coupler, etc. When the light distributor is a half mirror or a beam splitter, a lens system for adjusting light into parallel light is also included. Furthermore, if a return light affects an output, as in the case of a laser diode, an isolator, etc. is also included. Although not shown, a feedback system for driving the light source 62B1 may be mounted on the connection cable 24.

A reflecting member is, for example, a mirror, such as a mirror formed by evaporating aluminum, etc. onto the optical fiber 62C. Light supplied from the light source 62B1 passes through the detection subject portion 62D, and the light that has reached the end of the optical fiber 62C is returned to the light receiver 62B2 side.

Also, when the detection subject portion 62D changes the optical characteristics, such as absorption and conversion, the light receiver 62B2 detects a curved shape of the optical fiber 62C, specifically a direction and a magnitude of the bending, based on the changed optical characteristics.

The shape-computing circuit 62B3 computes the curved shape of a portion that is actually bent, based on a detection result of the light receiver 62B2. The optical characteristics are not limited to, for example, the light transmission amount, and may be, for example, a state of light, such as a spectrum or a polarized wave. That is, the light emitted from the light source 62B1 is a narrow band light such as a laser, and each of the detection subject portions 62D converts the light into lights of mutually-different wavelengths. Anything may be used as the detection subject portion 62D, as long as it detects optical characteristics corresponding to a light amount or a state of light, such as a spectrum and a polarized wave, etc., as described above. As a result, in the light receiver 62B2 and the shape computing circuit 62B3, it is possible to distinguish a change in the optical characteristics by each of the detection subject portions 62D.

Here, although an optical waveguide is described as the optical fiber 62C, it may be a film-like waveguide having a laminated structure in which light is confined and transmitted and the detection subject portion 62D has flexibility.

On the insertion portion 20, a magnetic position detection sensor including at least one magnetic coil as a sensor for detecting a reference position, can be mounted, rather than mount a fiber-shape sensor alone, in order to have a hybrid structure.

When a partial shape of the tubular system 12 can be changed by an operation, the operation amount sensor 64 detects shape information of the changeable part by detecting an amount of the operation. Specifically, the operation amount sensor 64 detects an operation amount of an operation of bending a bending portion which is a part of the insertion portion 20. This is to detect a movement of the rotating portion of a shaft of the operation knob 28 for performing the operation of bending the bending portion and a movement of a wire transmitting the rotation of the operation knob 28 to a shape deformation, by a sensor, such as an encoder.

For example, as shown in FIG. 8, the operation portion 22 is provided with the operation knob 28 for operating operation wires 80LR and 80UD for bending the bending portion of the insertion portion 20. The operation knob 28 has a left-right bending operation knob 28LR for bending the bending portion left-right, an up-down bending operation knob 28UD for bending the bending portion up-down, and a fixing knob (not shown) for fixing a position of the bent bending portion.

A bending operation driving portion (not shown) in the left-right direction driven by the operation of the left-right bending operation knob 28LR is connected to the left-right bending operation knob 28LR. A bending operation driving portion (not shown) in the up-down direction driven by the up-down bending operation knob 28UD is connected to the up-down bending operation knob 28UD. Here, the bending operation driving portion in the up-down direction, and the bending operation driving portion in the left-right direction, are provided in, for example, the operation portion 22. The bending operation driving portion in the left-right direction is connected to an operation wire 80LR inserted through the operation portion 22, and the flexible tube and the bending portion of the insertion portion 20. The operation wire 80LR is connected to the distal end portion of the bending portion. The bending operation driving portion in the up-down direction is connected to the operation wire 80UD inserted through the operation portion 22, and the flexible tube and the bending portion. The operation wire 80UD is a wire independent of the operation wire 80LR, and is connected to the distal end portion of the bending portion. The left-right bending operation knob 28LR bends the bending portion in the left-right direction, via the bending operation driving portion in the left-right direction and the operation wire 80LR. In addition, the up-down bending operation knob 28UD bends the bending portion in the up-down direction, via the bending operation driving portion in the up-down direction and the operation wire 80UD.

The operation knob 28 (the left-right bending operation knob 28LR and the up-down bending operation knob 28UD), the bending operation driving portion in the left-right direction, the operation wire 80LR, the bending operation driving portion in the up-down direction, and the operation wire 80UD, constitute a bending operation mechanism 82 for bending the bending portion.

The operation amount sensor 64 includes a bending operation amount detection portion 64A that detects a bending operation amount of the bending operation mechanism 82. Here, the bending operation amount of the bending operation mechanism 82 indicates an operation amount of the bending operation mechanism 82 (the operation wires 80LR and 80UD, and the operation knob 28) for bending the bending portion. In order for this bending operation amount detection portion 64A to detect the bending operation amount of the bending operation mechanism 82, a reading subject portion 64B, such as a linear scale, is provided at, for example, a proximal end portion of the operation wire 80LR and a proximal end portion of the operation wire 80UD. The reading subject portion 64B moves together with the operation wires 80LR and 80UD by the movement of the operation wires 80LR and 80UD. The bending operation amount detection portion 64A reads the reading subject portion 64B moving with the operation wires 80LR and 80UD, and detects the movement of the reading subject portion 64B. Thus, the bending operation amount detection portion 64A detects the movement of the operation wires 80LR and 80UD. The bending operation amount detection portion 64A is, for example, a linear encoder, and is provided, for example, inside the operation portion 22.

A bending operation amount detection circuit (not shown), configured in the information presentation system processing unit 14, detects a movement amount of the reading subject portion 64B (that is, movement amounts of the operation wire 80LR and the operation wire 80UD) based on a detection result detected by the bending operation amount detection portion 64A. Then, based on the detection result, bending operation amount information of the operation wire 80LR and the operation wire 80UD is computed, and the bending operation amount of the bending operation mechanism 82 is detected from the result so as to calculate bending operation amount information.

The reading subject portion 64B may be provided in the left-right bending operation knob 28LR and the up-down bending operation knob 28UD. In this case, the reading subject portion 64B is provided, for example, on an outer peripheral surface of the cylindrical left-right bending operation knob 28LR and an outer peripheral surface of the cylindrical up-down bending operation knob 28UD. In addition, the reading subject portion 64B may be provided on a surface of the left-right bending operation knob 28LR and a surface of the up-down bending operation knob 28UD. In this case, the bending operation amount detection portion 64A reads the reading subject portion 64B that rotates together with the left-right bending operation knob 28LR and the up-down bending operation knob 28UD, and detects a rotation of the reading subject portion 64B. Thus, the bending operation amount detection portion 64A detects the rotation of the left-right bending operation knob 28LR and the up-down bending operation knob 28UD. The bending operation amount detection portion 64A is, for example, a rotary encoder. The bending operation amount detection circuit (not shown) detects an amount of movement of the reading subject portion 64B, that is, amounts of rotation of the left-right bending operation knob 28LR and the up-down bending operation knob 28UD, based on the detection result detected by the bending operation amount detection portion 64A. Based on this detection result, the bending operation amount information of the left-right bending operation knob 28LR and the up-down bending operation knob 28UD may be computed.

The bending portion does not necessarily have to be bendable up-down and left-right. For example, the bending portion may be configured to be able to bend only up-down or only left-right. In this case, the operation amount sensor 64 detects the bending operation amount in the up-down direction or the bending operation amount in the left-right direction of the bending operation mechanism 82. The bending operation amount detection circuit (not shown) may compute the respective bending operation amount information.

The posture sensor 66 detects postural information on a rear end side of the insertion portion 20 through, for example, a magnetic coil, a gyro sensor, or an acceleration sensor, etc., provided in the operation portion 22. That is, this posture sensor 66 detects an inclination of the insertion portion 20 and a rotation amount of the insertion portion 20 by the operator.

The insertion situation observation sensor 68 includes, for example, a camera for observing the insertion situation, etc., and performs predetermined image processing on an image, which is an output of this insertion situation observation sensor 68, so as to detect an orientation and position information of the insertion subject 26, and estimates the degree of pain from facial expressions of the insertion subject 26. Here, the predetermined image processing includes processing of recognizing and determining characteristics of an imaging target by pattern matching, determination processing using similarity by deep learning, and determination processing of a place by luminance or color difference, etc.

The insertion subject posture sensor 70 is, for example, a magnetic position detection sensor including a plurality of transmission coils attached to the insertion subject 26 and the receiving antenna 60B, and detects postural information of the insertion subject 26. That is, this insertion subject posture sensor 70 detects a position, an inclination, and a direction of the insertion subject 26 from, for example, position information at three points based on an output of the magnetic position detection sensor.

A weight-detection sensor 72 is, for example, a strain sensor or a pressure sensor which can detect weight distribution, which is placed on the examination table 46, such as a bed, and detects an orientation and position information of the insertion subject 26. That is, this weight-detection sensor 72 detects a weight movement of the insertion subject 26 on the examination table 46.

In addition, the insertion subject state monitoring monitor 74 is, for example, a monitoring device attached to a finger of the insertion subject 26 to detect a pulse, etc., and monitors a state of the insertion subject 26, such as a pulse rate and a breathing state of the insertion subject 26.

The insertion amount detection sensor 76 is an optical sensor, etc. installed at an entrance of the insertion subject 26 (mouth, anus, lung, examination port, etc.) which detects the insertion amount of the insertion portion 20 into the insertion subject 26. That is, the insertion amount detection sensor 76 optically reads an image or a number written on a surface of the insertion portion 20, or a surface speckle image of the insertion portion 20. Furthermore, the insertion amount detection sensor 76 can also detect the rotation amount of the insertion portion 20. The insertion amount detection sensor 76 may use, for example, a method of reading, via an encoder, a movement of a roller brought into contact with the insertion portion 20.

The image sensor 78 arranged at the distal end of the insertion portion 20 can be used as a detection device that performs predetermined image processing on a captured image by an image processing circuit (not shown) configured in the tubular system control circuit 30, thereby detecting that the insertion portion 20 has started insertion into the insertion subject 26, an observation position (extracting and detecting a part or a characteristic shape or pattern) of the insertion subject 26, etc., and any abnormal part, etc. The image processing circuit (not shown) can also detect other information that can be extracted from an image, such as the type of treatment. Here, the predetermined image processing includes processing of recognizing and determining characteristics of an imaging target by pattern matching, determination processing using similarity by deep learning, and determination processing of a place by luminance or color difference, etc.

The tubular system function selection and operation circuit 52 can detect patient information for control of the tubular system 12 and various setting conditions such as lighting, suction, and scavenging, based on input information for control of the tubular system 12.

Furthermore, the switching dial 42 operated by the operator as described in the first embodiment serves as a detection device that detects the presence or absence of conscious presentation by the operator.

Based on at least one output of such a detection device, the state detection circuit 54 detects the state of the tubular system 12 and/or the insertion subject 26. Based on at least one or more states detected by this state detection circuit 54, the presentation information generation circuit 56 generates specification information which specifies selection and a presentation time of the presentation information 38 to be presented to the non-operator presentation display 18.

Figure 9A:
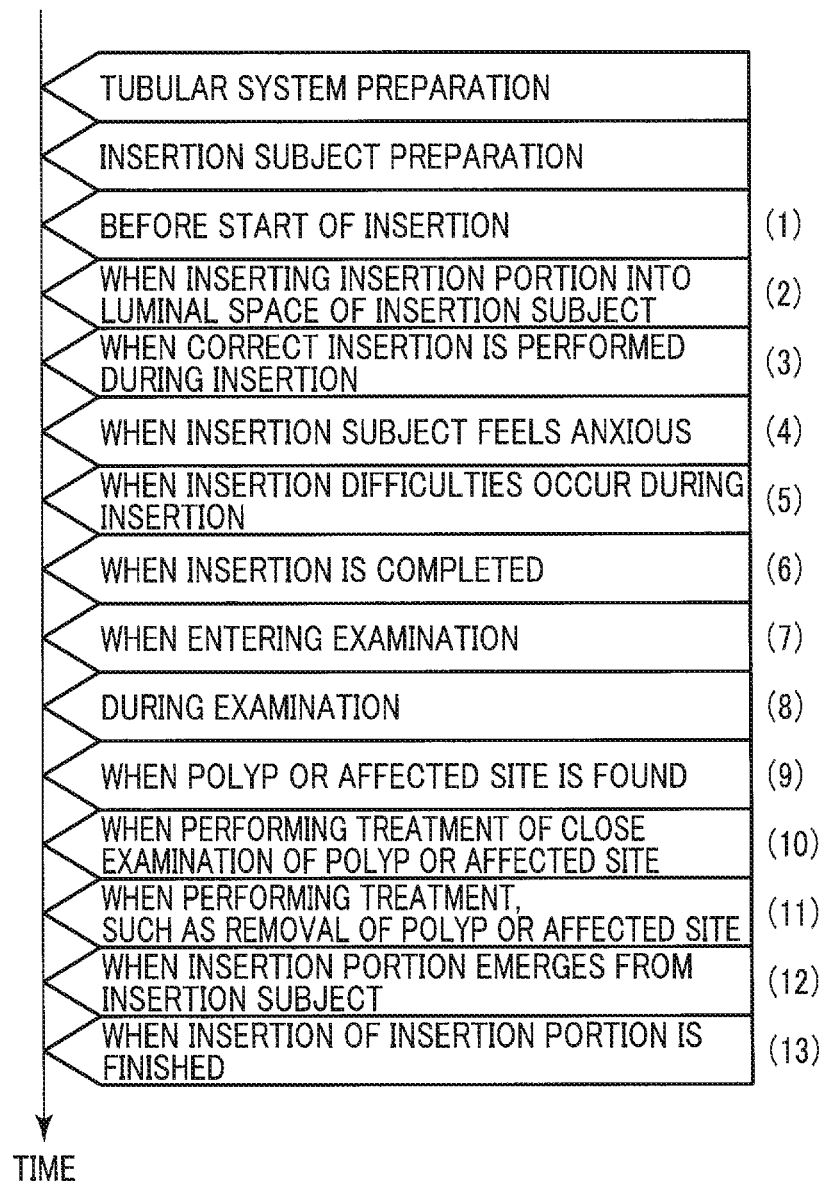
FIG. 9A is a diagram showing the kind of presentation information is presented at certain times.
Figure 9B:
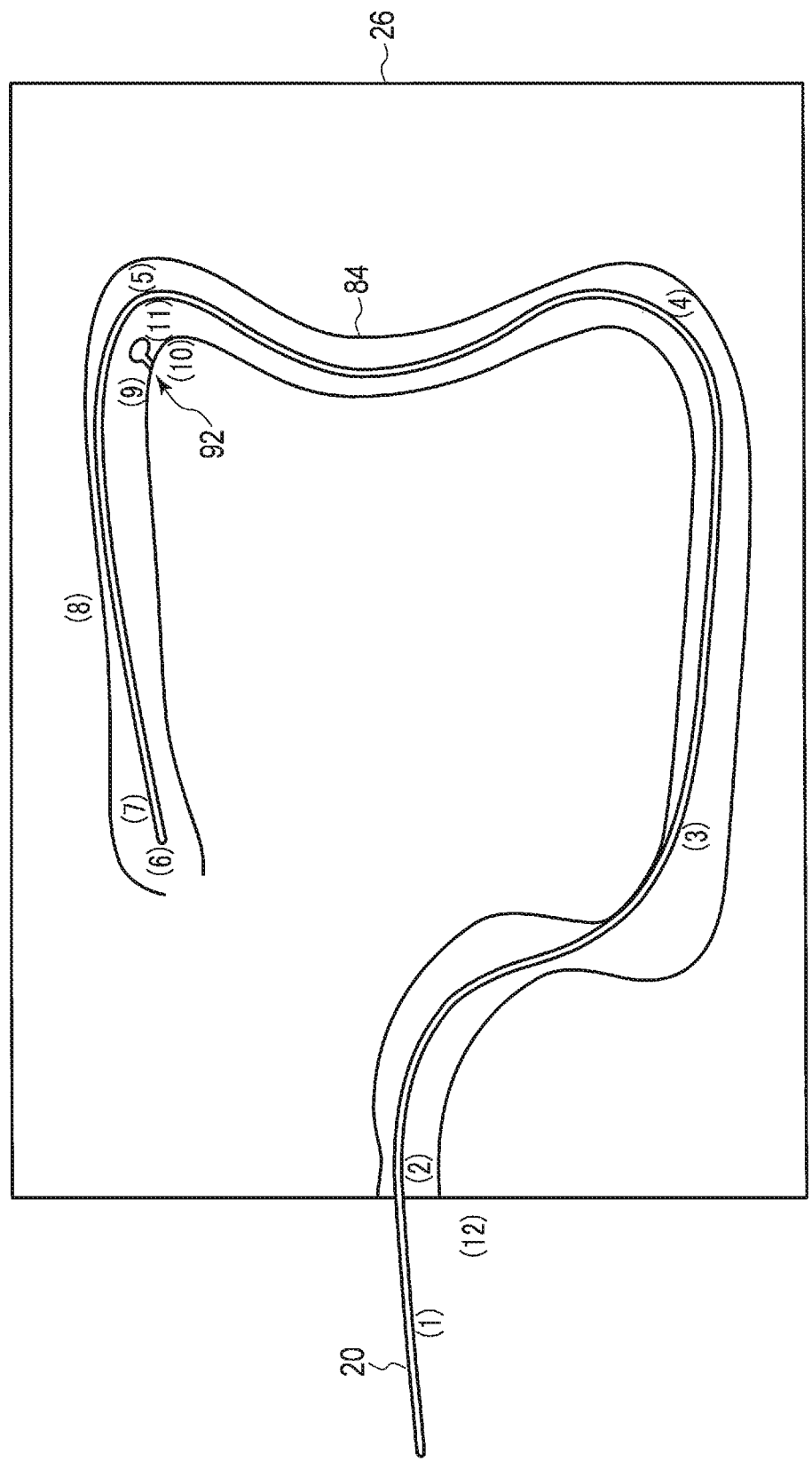
FIG. 9B is a diagram showing a relationship between the timing at which presentation information is presented and a distal end position of the insertion portion in an insertion subject.

FIG. 9A shows the kind of presentation information 38 that can be presented at each possible timing, and FIG. 9B shows a relationship between the timing and a position of the distal end portion of the insertion portion 20 in a large intestine 84 which is a luminal space of the insertion subject 26. FIGS. 10A and 10B show an example of the state of the tubular system 12 and/or the insertion subject 26 detected by the state detection circuit 54, and the selection of the presentation information 38 by the presentation information generation circuit 56, at each timing.

A timing (1) is a time before start of the insertion of the insertion portion 20 into the luminal space of the insertion subject 26. Before this timing (1), there is a period during which a preparation of the tubular system 12 and a preparation of the insertion subject 26 are performed.

At this timing (1), the state detection circuit 54 can detect that a light switch is turned on as the state of the tubular system 12, based on an output of the tubular system function selection and operation circuit 52, for example. Alternatively, based on the observation image by the image sensor 78, the state detection circuit 54 can detect that the insertion portion 20 is outside the insertion subject 26 and has moved out of a stop state, as the state of the tubular system 12. Based on the output of the insertion situation observation sensor 68, the state detection circuit 54 can detect that the insertion subject 26 is placed on the examination table 46 as the state of the tubular system 12 and the insertion subject 26, and can detect that the operator is holding the insertion portion 20 as the state of the tubular system 12. When any one of these states is detected by the state detection circuit 54, the presentation information generation circuit 56 determines that it is the timing (1), and selects one or more of an insertion start, an explanation of a hospital, an explanation of an operator, an explanation of an examination, and relaxing music, etc. among the plurality of pieces of presentation information 38 stored in the storage medium 32, as the presentation information 38 to be presented to the non-operator presentation display 18.

A timing (2) is when the insertion portion 20 is inserted into the luminal space of the insertion subject 26. At this timing (2), the state detection circuit 54, for example, can detect that the insertion portion 20 has entered the insertion subject 26 from the outside of the insertion subject 26, as the state of the tubular system 12, based on the observation image by the image sensor 78. Alternatively, the state detection circuit 54 can detect that the insertion portion 20 has been set at a luminal space entrance of the insertion target 26, as the state of the tubular system 12, based on an output of the curved-shape detection sensor 62 or an output of the distal end position detection sensor 60. In addition, the state detection circuit 54 can detect that the insertion portion 20 has been inserted into the insertion subject 26, as the state of the tubular system 12, based on the output of the insertion situation observation sensor 68. When any one of these states is detected by the state detection circuit 54, the presentation information generation circuit 56 determines that it is the timing (2), and can select, from among the plurality of pieces of presentation information 38 stored in the storage medium 32, the start of the insertion or the explanation to promote relaxation, as the presentation information 38 to be presented to the non-operator presentation display 18.

A timing (3) is when a correct insertion is performed while inserting the insertion portion 20 into the luminal space of the insertion subject 26. At this timing (3), the state detection circuit 54 can detect, for example, based on the output of the curved-shape detection sensor 62, the operation amount sensor 64, or the insertion situation observation sensor 68 (this may be the insertion subject posture sensor 70 or the weight-detection sensor 72), that an arrangement and a shape of the insertion portion 20 in the insertion subject 26 have a normal shape pattern or are appropriate in terms of length and time of insertion into the insertion subject 26 as the state of the tubular system 12, and can also detect the absence of an excessive load (force) on the insertion subject 26 as the state of the tubular system 12 and the insertion subject 26. When any one of these states is detected by the state detection circuit 54, the presentation information generation circuit 56 determines that it is the timing (3), and can select, from among the plurality of pieces of presentation information 38 stored in the storage medium 32, the explanation of the insertion situation or the explanation to promote relaxation as the presentation information 38 to be presented to the non-operator presentation display 18.

A timing (4) is a time that the insertion subject 26 can possibly feel anxious. At this timing (4), the state detection circuit 54 can detect, for example, that the pulse and the breathing state of the insertion subject 26 are normal but have risen to the extent of feeling anxious, as the state of the insertion subject 26, based on the output of the insertion subject state monitoring monitor 74. When such a state is detected by the state detection circuit 54, the presentation information generation circuit 56 determines that it is the timing (4), and selects the explanation to promote relaxation among the plurality of pieces of presentation information 38 stored in the storage medium 32, as the presentation information 38 to be presented to the non-operator presentation display 18.

Figure 11A:
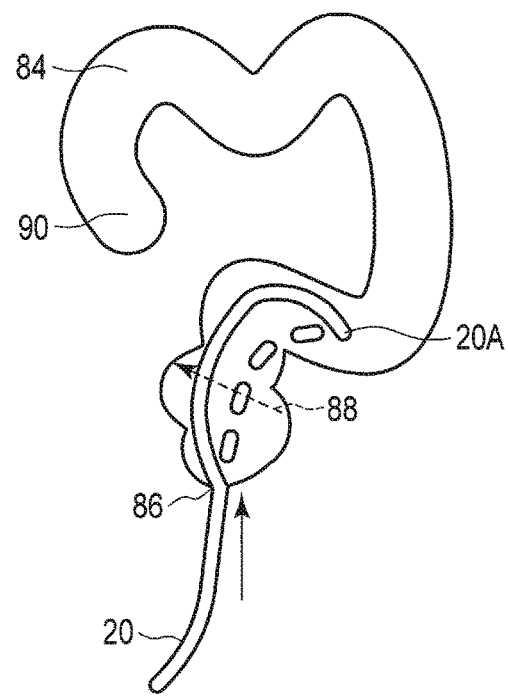
FIG. 11A is a diagram for explaining an example in which insertion of the insertion portion is inhibited.
Figure 11B:
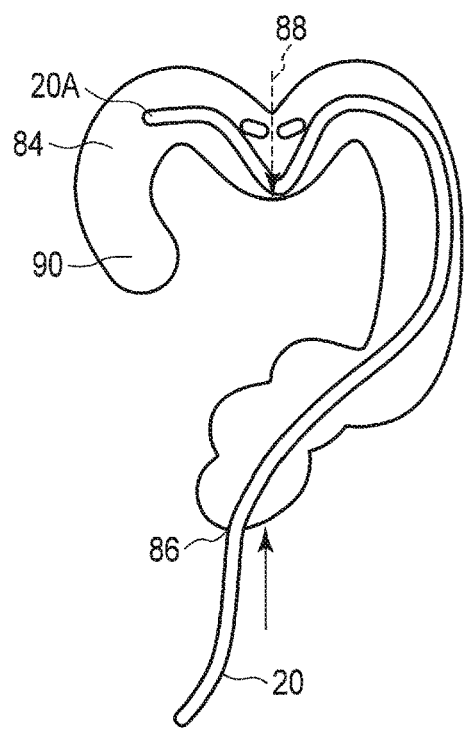
FIG. 11B is a diagram for explaining an example in which insertion of the insertion portion is inhibited.

A timing (5) is a situation where it is difficult to insert the insertion portion 20 during insertion. At this timing (5), the state detection circuit 54 can, for example, based on the output of the curved-shape detection sensor 62, the operation amount sensor 64, or the insertion situation observation sensor 68 (this may be the insertion subject posture sensor 70 or the weight-detection sensor 72), determined from the arrangement and shape of the insertion portion 20 inside the insertion subject 26, detects that a middle of the insertion portion 20 is deflected and propulsion (insertion) to the luminal space end of the distal end is inhibited, as the state of the tubular system 12. That is, as shown in FIGS. 11A and 11B, for example, in a situation where the insertion portion 20 is inserted from an anus 86, which is an entrance, with respect to the large intestine 84 as indicated by a broken line, when the insertion portion 20 is pushed in as indicated by a solid arrow in the figure so as to further insert the insertion portion 20, a pushing force of a pushing operation may not be transmitted to the distal end 20A of the insertion portion 20, and the insertion portion 20 may be deflected as indicated in the figure by a broken arrow 88. When such a deflection occurs, the distal end 20A does not move in the direction of a cecum 90 and substantially remains at that position, as indicated by a solid line in the figure. When the state detection circuit 54 detects such a state, the presentation information generation circuit 56 determines that it is the timing (5), and selects, as the presentation information 38 to be presented to the non-operator presentation display 18, a sign for requesting a postural change, etc., among the plurality of pieces of presentation information 38 stored in the storage medium 32.

In addition, at this timing (5), the deflected insertion portion 20 may push up a wall of the large intestine, which may cause pain to a patient who is the insertion subject 26. A sound emitted due to the pain can be acquired by a microphone (not shown), and the state detection circuit 54 can detect such a state from the voice emitted by the insertion subject 26. In this manner, the state detection circuit 54 can also recognize words emitted by the insertion subject 26, and a conversation with the operator, by a speech recognition technology to detect the state of the insertion subject 26 or the insertion situation of the insertion portion 20.

A timing (6) is when the insertion of the insertion portion 20 is completed. Also, a timing (7) is when an examination is started. The timing (6) and the timing (7) are similar. That is, the point at which the insertion of the insertion portion 20 is completed is the point at which the examination can be started. At this timing (6) or timing (7), the state detection circuit 54 can, for example, based on the output of the curved-shape detection sensor 62 and the insertion situation observation sensor 68, or the observation image by the image sensor 78, detect that the arrangement and shape of the insertion portion 20 in the insertion subject 26 and/or the observation image confirm a small intestinal entrance, as the state of the tubular system 12. When such a state is detected by the state detection circuit 54, the presentation information generation circuit 56 determines that it is the timing (6) or (7), and selects the explanation of the examination among the plurality of pieces of presentation information 38 stored in the storage medium 32, as the presentation information 38 to be presented to the non-operator presentation display 18.

A timing (8) is when the examination is underway. At this timing (8), the state detection circuit 54, for example, can detect, based on the output of the curved-shape detection sensor 62 and the insertion situation observation sensor 68, or the observation image by the image sensor 78, the time of an inverted visual observation shape of the anus 86 of the insertion portion 20 in the insertion subject 26, and/or when the insertion portion 20 itself can be recognized in the observation image, as the state of the tubular system 12. When such a state is detected by the state detection circuit 54, the presentation information generation circuit 56 determines that it is the timing (8), and selects the explanation of the examination status among the plurality of pieces of presentation information 38 stored in the storage medium 32, as the presentation information 38 to be presented to the non-operator presentation display 18.

A timing (9) is when a polyp or an affected site is found. At this timing (9), the state detection circuit 54, for example, can detect that a polyp shape and/or the affected site have been recognized as the state of the tubular system 12 and the state of the insertion subject 26, based on the observation image by the image sensor 78. When such a state is detected by the state detection circuit 54, the presentation information generation circuit 56 determines that it is the timing (9), and selects the explanation of the examination status among the plurality of pieces of presentation information 38 stored in the storage medium 32, as the presentation information 38 to be presented to the non-operator presentation display 18.

A timing (10) is when performing a treatment of a close examination of the polyp or the affected site. A timing (11) is when performing a treatment, such as removal of the polyp or the affected site. At these timings (10) or (11), the state detection circuit 54, for example, can detect that forceps for biopsy is captured in the observation image, as the state of the tubular system 12, based on the observation image by the image sensor 78. When such a state is detected by the state detection circuit 54, the presentation information generation circuit 56 determines that it is the timing (10) or (11), and selects the explanation of the examination status or the treatment status among the plurality of pieces of presentation information 38 stored in the storage medium 32, as the presentation information 38 to be presented to the non-operator presentation display 18.

A timing (12) is when the insertion portion 20 emerges from the insertion subject 26 (a case in which, when a reference position of an insertion length is set to the position of the anus, the length is below the reference value, is also possible). At this timing (12), the state detection circuit 54, for example, can detect that the insertion portion 20 has emerged from the insertion subject 26 as the state of the tubular system 12, based on the output of the insertion situation observation sensor 68 and/or the observation image by the image sensor 78. When such a state is detected by the state detection circuit 54, the presentation information generation circuit 56 determines that it is the timing (12), and selects the explanation after completion among the plurality of pieces of presentation information 38 stored in the storage medium 32, as the presentation information 38 to be presented to the non-operator presentation display 18.

Then, a timing (13) is when the insertion of the insertion portion 20 into the lumen of the insertion subject 26 is finished. At this timing (13), contrary to the above timing (1), the state detection circuit 54, for example, can detect that the light switch is turned off; the insertion portion 20 is outside the insertion subject 26 and is stopped; and the operator releases the insertion portion 20 and the insertion subject 26 is lowered from the examination table 46, etc. When anyone of these states is detected by the state detection circuit 54, the presentation information generation circuit 56 determines that it is the timing (13). However, at this timing (13), since it is no longer necessary to present the presentation information 38 to the non-operator presentation display 18, the selection of the presentation information 38 is not performed.

The presentation information selection and switching circuit 34 switches between the selection and presentation period of the presentation information 38, and the presentation method to the non-operator presentation display 18, according to the selection by the presentation information output selection circuit 58. In this case, various pieces of presentation information 38 can be selectively presented by the detection device used. However, it is not always necessary to present the selected presentation information 38. For example, depending on the examination or treatment, there is also a case where the information may not be presented to a non-operator including the insertion subject 26. Furthermore, when the selected presentation information 38 is presented by the non-operator presentation display 18, the presentation method also differs depending on the non-operator, including the insertion subject 26. For example, even if the presentation information 38 is presented to a visually-impaired person by the monitor 48, or the presentation information 38 is presented to a hearing-impaired person by the speaker 50, Accordingly, the presentation information output selection circuit 58 enables the operator to select the presentation information 38 to be presented to the non-operator, and also select the presentation method (a language, an output destination (the monitor 48, the speaker 50, etc.) etc.). That is, as shown in FIG. 2, for the presentation information content selection display 44 of the operator display 16, the presentation information output selection circuit 58 produces a display for whether to present each of the plurality of pieces of presentation information 38 stored in the storage medium 32, and performing the selection as to the presentation method of these plurality of pieces of presentation information 38. Then, according to a touch panel operation of the operator display 16 or the operations of the switching dial 42 and the selection button 40 of the operation portion 22 by the operator, it is possible to select whether or not to present each presentation information 38 and the presentation method. Alternatively, this presentation information output selection circuit 58 may be configured so as to automatically determine and select, by using a medical history or information input in advance, instead of via the selection by the operator.

The switching of the presentation information in the presentation information generation circuit 56 need not be necessarily performed at the above timing. For example, by providing each piece of presentation information 38 stored in the storage medium 32 with attribute information (such as the time until completion of presentation, a priority, and a duplication possibility), the presentation information generation circuit 56 can specify the presentation time of the presentation information 38 to be presented to the non-operator presentation display 18 according to the attribute information.

Figure 13:
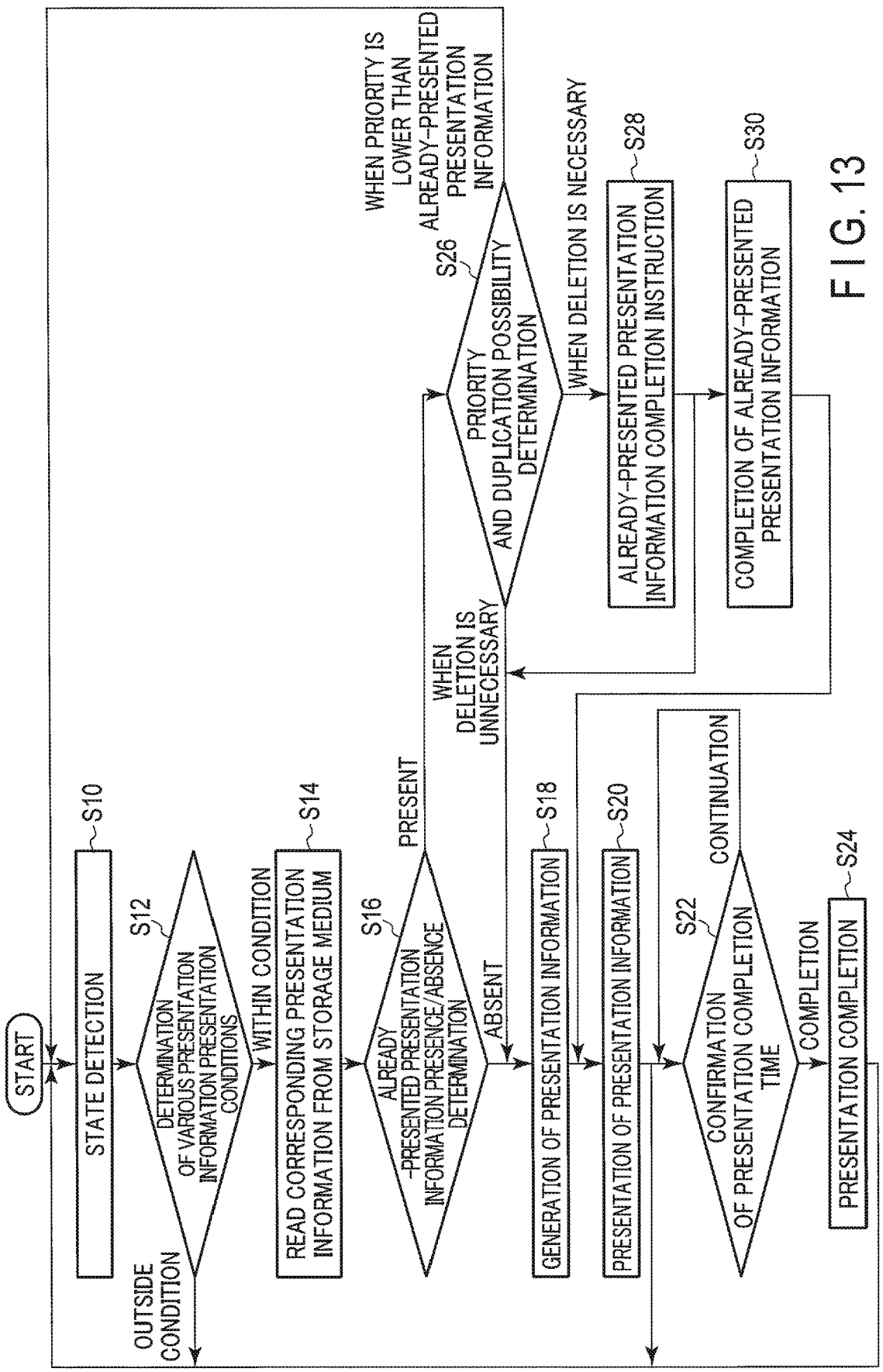
FIG. 13 is a diagram showing a flowchart for explaining operations of a presentation information generation circuit and a presentation information selection and switching circuit.

That is, as shown in FIG. 13, if the state detection circuit 54 detects the state of the tubular system 12 and/or the insertion subject 26 (step S10), the presentation information generation circuit 56 determines whether the detected state matches the various presentation information presentation conditions as shown in FIGS. 10A and 10B (step S12). Then, if it is determined that the detected state does not match the condition (that is, if it is out of the condition), the presentation information generation circuit 56 waits for a detection of the next state.

On the other hand, if it is determined that the condition is met (that is, within the condition), the presentation information generation circuit 56 reads information, such as a type (e.g., an insertion start, etc.) and attribute information of the corresponding presentation information 38, from the storage medium 32 (step S14). Then, the presentation information generation circuit 56 determines whether or not some presentation information 38 has already been presented by the non-operator presentation display 18; that is, performs determination of presence/absence of already-presented presentation information (step S16). Here, if it is determined that there is no presentation information already presented, the presentation information generation circuit 56 selects the presentation information 38, read in the above step S14, as the presentation information 38 to be presented to the non-operator presentation display 18, generates specification information which specifies a type thereof, a presentation time including a time until a completion of the presentation, and an output method selected by the presentation information output selection circuit 58, and supplies it to the presentation information selection and switching circuit 34 (step S18). Thereby, the presentation information selection and switching circuit 34 reads the content of the selected presentation information 38 (e.g., either a display or a vocal instruction of "insertion is about to be started" in a selected language, etc.) from the storage medium 32, and the content of the presentation information 38 will be presented by the non-operator presentation display 18 (step S20).

Thereafter, the presentation information generation circuit 56 waits for detection of the next state. On the other hand, if the presentation information selection and switching circuit 34 starts presentation of the presentation information 38, it confirms a time of completion of the presentation for said presentation information 38 during a continuation period until the completion of the presentation, based on the above-described specification information which specifies the presentation time (step S22). Then, when it is time to complete the presentation, the presentation information selection and switching circuit 34 completes the presentation of the presentation information 38 (step S24).

When it is determined in the above step S16 that the already-presented presentation information is present, the presentation information generation circuit 56 determines a priority and a duplication possibility, based on the attribute information of the presentation information 38 read in the above step S14 (step S26). Here, if it is determined that the presentation information 38 read in the above step S14 has a lower priority than the already-presented presentation information, the presentation information generation circuit 56 will ignore said read presentation information 38 and wait for detection of the next state.

On the other hand, in the above step S26, if it is determined that the presentation information 38 read in the above step S14 has a higher priority than the presentation information already presented, but duplication with said presentation information is possible, deletion of the presentation information already presented is unnecessary, so the presentation information generation circuit 56 will proceed to the above step S18. Thus, in this case, the presentation information generation circuit 56 selects the presentation information 38 read in the above step S14, generates specification information specifying a type, a presentation time, and an output method thereof, and supplies the specification information to the presentation information selection and switching circuit 34. Thereby, the presentation information selection and switching circuit 34 presents the content of the selected presentation information 38, in addition to the presentation of the presentation information already presented, by the non-operator presentation display 18.

On the other hand, in the above step S26, if it is determined that the presentation information 38 read in the above step S14 has a higher priority than the presentation information already presented, and a duplication with said presentation information is not possible, it becomes necessary to delete mentioned above the presentation information, and the presentation information generation circuit 56 instructs the presentation information selection and switching circuit 34 to complete the presentation of the said information (step S28). Then, the presentation information generation circuit 56 proceeds to the above step S18 to select the presentation information 38 read in the above step S14, generates specification information specifying a type, a presentation time, and an output method thereof, and supplies the specification information to the presentation information selection and switching circuit 34. The presentation information selection and switching circuit 34 completes the presentation of the already-presented presentation information 38 to the non-operator presentation display 18, in response to the instruction to complete the presentation of the presentation information already presented in the above step S28 (step S30). Then, in the above step S20, the presentation information 38 will be newly presented to the non-operator presentation display 18 according to the instruction of the presentation information generation circuit 56.

In addition, the operator may forcibly interrupt such a presentation of the presentation information 38 to the non-operator presentation display 18 at a timing of his/her choosing. For that purpose, for example, a presentation stop button 94 is provided in the operation portion 22 of the tubular system 12. When the state detection circuit 54 detects that the presentation stop button 94 has been operated by the operator, the presentation information generation circuit 56 instructs the presentation information selection and switching circuit 34 to complete the presentation of the presentation information already presented. Thus, the presentation information generation circuit 56 can function as a presentation stop circuit that forcibly interrupts the presentation of the presentation information 38 to the non-operator presentation display 18, through the operation of the operator. Such presentation stop button 94 and presentation stop circuit are similarly applicable to the above-described first embodiment.

As described above, the information presentation system 10, as the information presentation system according to the present second embodiment, can obtain the same or similar effect as that of the above-described first embodiment.

Furthermore, in the present second embodiment, the state detection circuit 54 that detects the state of the tubular system 12 and/or the insertion subject 26, and the presentation information generation circuit 56 that generates specification information which specifies selection and a presentation time of the presentation information 38 to be presented to the non-operator presentation display 18, based on at least one or more states detected by the state detection circuit 54, are further included. The presentation information selection and switching circuit 34 performs selection of the presentation information 38 and switching of the presentation period in accordance with the specification information generated by the presentation information generation circuit 56.

Therefore, even if the operator does not specify the selection and the presentation time of the presentation information 38, it is possible to present appropriate presentation information 38 based on the state of the tubular system 12 and/or the insertion subject 26. This allows the operator to operate the tubular system 12 intensively relatively higher degree of focus, and perform the insertion operation, examination, and treatment relatively more safely.

Here, a presentation stop circuit may be further provided, which forcibly interrupts the presentation of the presentation information 38 to the non-operator presentation display 18 by the operation of the operator.

Thereby, when presentation information which has automatically started to become presented is not appropriate, or when the operator has mistakenly selected incorrect presentation information, it is possible to interrupt the presentation of said information.

In addition, the information presentation system 10, as an information presentation system according to the present second embodiment, includes the presentation information output selection circuit 58 that selects the presentation information 38 to be presented to the non-operator and the presentation method (a language, an output destination (the monitor 48, the speaker 50, etc.)). The presentation information generation circuit 56 generates specification information which specifies selection, and a presentation period of the presentation information 38, and a presentation method to the non-operator presentation display 18, in accordance with the selection by the presentation information output selection circuit 58. The presentation information selection and switching circuit 34 also switches the selection and the presentation period of the presentation information 38, and the presentation method to the non-operator presentation display 18, in accordance with the specification information generated by the presentation information generation circuit 56.

Accordingly, necessary presentation information 38 can be changed according to the state of the insertion subject 26. The state of the insertion subject 26 includes a non-impaired person, a visually-impaired person, a hearing-impaired person, and a case where the presentation information 38 is selectively required depending on a specific medical condition, etc. The selection, the presentation period, and the presentation method of the presentation information 38 may be automatically determined in the information presentation system 10 by using a medical history or information input in advance. Also, if the language that can be understood differs between the non-operator including the insertion subject 26 and the operator, by switching the language, a sense of security regarding the insertion subject 26 can be enhanced, and the insertion, observation and treatment of the tubular system 12 can be relatively safer and relatively easier.

Here, the presentation information 38 can include at least one of: an explanation at the start of an insertion of the insertion portion 20 into the insertion subject 26, an explanation of a hospital, an explanation of an operator, an explanation of an examination, an explanation of an insertion situation, a sign for requesting a postural change to the insertion subject 26, an explanation to promote relaxation, an explanation of an examination status or a treatment status, and an explanation after completion.

Thereby, the insertion subject 26 can obtain an understanding about the insertion and the insertion subject 26 can have a relative sense of security from the presented presentation information 38, and can be in a relatively relaxed state. Alternatively, if the insertion subject 26 is an animal, a non-operator, such as an owner, via understanding the various pieces of presentation information 38, can help bring the insertion subject 26 into a relatively relaxed state, and can put the insertion subject 26 in a relatively relaxed state. Accordingly, the presentation of the presentation information 38 can make it possible to perform insertion of the tubular device into the insertion subject 26, examination, and treatment relatively more safe and relatively easier.

The state detection circuit 54 can detect a state of the tubular system 12 and/or the insertion subject 26 based on an output of at least one of: a distal end position detection sensor that detects a distal end position of the insertion portion 20; the curved-shape detection sensor 62 that detects a curved-shape of the insertion portion 20; the operation amount sensor 64 that detects an operation amount of an operation of bending the insertion portion 20; the posture sensor 66 that detects a posture on a rear-end side of the insertion portion 20; the image sensor 78 provided in the tubular system 12; the insertion situation observation sensor 68 (a camera, etc.) that observes an insertion situation, the insertion subject posture sensor 70 that detects a posture of the insertion subject 26; the weight-detection sensor 72 that detects a weight movement of the insertion subject 26 on the examination table 46; the switching dial 42 operated by the operator; the tubular system function selection and operation circuit 52 that inputs information necessary for control of the tubular system 12; the insertion subject state monitoring monitor 74 that monitors a state of the insertion subject 26; the insertion amount detection sensor 76 that detects an insertion amount of the insertion portion 20 into the insertion subject 26; and a microphone that detects a sound generated by the insertion subject 26.

Thus, by using various detection devices, without the need for the operator to act, information required by the non-operator (including the insertion subject 26), information for the insertion subject 26 to relax, or information for a postural change to support an insertion, etc., can be automatically detected, generated, and/or presented. Accordingly, the operator does not need to focus on the information presentation to the non-operator, and can concentrate on insertion, examination, and/or treatment. Therefore, the insertion of the insertion portion 20 into the insertion subject 26, operation, and/or treatment can be performed relatively more safely and relatively easily. In addition, doctors with less experience tend to concentrate comparatively more on the insertion of the insertion portion 20, and may have a slight lack of care for the insertion subject 26. As a result, a sense of satisfaction with the examination in the non-operator including the insertion subject 26 may be weakened, which may not lead the insertion subject 26 to undergo continuous medical examination, and eventually risks possible delay to early detection of a disease such as cancer. However, by using the information presentation system 10 of the present embodiment, the non-operator, including the insertion subject 26, can obtain a relative degree of satisfaction with the examination, thereby reducing such a concern.

In addition, the presentation information generation circuit 56 selects the presentation information 38 to be presented to the non-operator presentation display 18 from among the plurality of pieces of presentation information 38 stored in advance in the storage medium 32 by determining whether at least one or more states detected by the state detection circuit 54 match a predetermined setting condition.

Accordingly, the presentation information generation circuit 56 can extract information to be presented from the situation of the insertion subject 26 and the situation of the tubular system 12, acquired from the detection device, and can provide information in a range assumed by the information presentation system 10. This configuration enables the provision of accurate insertion, examination, and/or treatment information to the insertion subject 26, and can make the state of the insertion subject 26 to be in an expected state in advance. This enables relatively safe and relatively easy operation (insertion, examination, and/or treatment, etc.) of the tubular system 12.

The presentation information 38 can be presented on at least one of the following timings: before start of insertion of the insertion portion 20; when the insertion portion 20 is inserted into a luminal space of the insertion subject 26; when a correct insertion is performed during the insertion of the insertion portion 20; when the insertion subject 26 feels anxious; when it is difficult to insert during the insertion of the insertion portion 20; when the insertion of the insertion portion 20 is completed; when entering an examination; during the examination; when a polyp or an affected site is found; when performing a treatment of a close examination of the polyp or the affected site; when performing a treatment, such as removal of the polyp or the affected site; when the tubular system 12 emerges from the insertion subject 26; and when the insertion of the insertion portion 20 is finished.

Accordingly, for the non-operator including the insertion subject 26, at each timing, accurate insertion, examination, and/or treatment information can be provided, the state of the insertion subject 26 can be delivered to an expected state in advance, and relatively safe and relatively easy operation (insertion, examination, and/or treatment, etc.) of the tubular system 12 can be performed.

The tubular system 12 is an endoscope comprising an image sensor provided at the distal end of the insertion portion 20 and the operator display 16 that displays an image captured by the image sensor, and the non-operator presentation display 18 can include the monitor 48 separate from the operator display 16.

Endoscopy may involve lowering the patient's awareness by anesthesia to reduce the patient's pain. This sedation carries various risks in the form of the medicine itself and the fact that the pain during insertion may not be transmitted to the operator. Medical costs can also be high. On the other hand, by introducing the information presentation system 10 as the information presentation system according to the present second embodiment, the patient can reduce the awareness of the insertion. Thus, the probability of performing an operation that causes pain to the patient is reduced, and the use of anesthesia can be eliminated. Therefore, the information presentation system 10 according to the present second embodiment can provide a relatively safe and relatively easy examination without need for sedation.

Although the present invention has been described above based on some embodiments, the present invention is not limited to the above-described embodiments, and various modifications and applications are possible without departing from the scope of the present invention.

For example, in the above-described embodiments, the case where the operator, such as a doctor, holds the insertion portion 20 and performs the insertion operation to the insertion subject 26 has been described by way of example, but the present invention is also applicable to the case where an insertion operation is performed by a robot system as shown in FIG. 14. In this robot system, the insertion portion 20 is inserted into the insertion subject 26 by a tubular system driving device 96. The tubular system driving device 96 is, for example, connected to a tubular system controller 98 arranged in another room, etc., via a tubular system electrical wiring 100. As a matter of course, the tubular system driving device 96 may be wirelessly connected to the tubular system controller 98. The tubular system controller 98 includes the operator display 16 and a tubular system control grip portion 104, as an interface with an operator 102. In response to an operation of the tubular system control grip portion 104 by the operator 102, the tubular system controller 98 controls the driving of the tubular system driving device 96 so that it inserts the insertion portion 20 into the insertion subject 26.

In addition, for communication between the insertion subject 26 and the operator 102, a microphone 106 can be provided on or near the examination table 46, and a voice emitted by the insertion subject 26 is transmitted to a headphone 108, worn by the operator 102, via a microphone wiring 110 and the tubular system controller 98. In its reverse direction, a voice emitted by the operator 102 can be acquired by an operator side microphone 112, and, via a presentation information electrical wiring 114, the acquired voice is output from the speaker 50 of the non-operator presentation display 18 arranged at a position viewable by the insertion subject 26. The tubular system controller 98 includes the information presentation system processing unit 14 as described in the above embodiments, and can present the presentation information 38 as described in the above embodiments courtesy of the non-operator presentation display 18.

As described above, when a distance between the insertion subject 26 and the operator 102 is large, it is difficult for the operator 102 to speak to the insertion subject 26 directly, and therefore the operator 102 concentrates on the operation. Thus, by presenting information by the information presentation system 10 as in the above-described embodiments (in particular, the information presentation system 10 pre-programmed as in the above-described second embodiment), insertion, examination and treatment can be made relatively safely and relatively easily.

The present invention is also applicable to an insertion of the insertion portion 20 for inspection of a jet engine as shown in FIG. 15. The jet engine which is the insertion subject 26 includes a fan 26A, a compressor 26B, and a combustion chamber 26C, etc. An operation portion, such as the fan 26A, needs to be operated according to inspection conditions. The operator 102 cannot operate the operation portion of the jet engine because the operator 102 performs the insertion operation of the insertion portion 20 while operating a tubular system control device 116 connected to the information presentation system processing unit 14. Thus, there is another driver 118, a non-operator, who operates the operation portion of the jet engine which is the insertion subject 26.

In such a case, the information presentation system 10 of the above embodiments, in particular, of the above second embodiment can be applied. That is, the driver 118 (the non-operator) holds the monitor 48 of the non-operator presentation display 18, and wears the speaker 50 of the non-operator presentation display 18 the non-operator as a headphone. Then, via the information presentation system processing unit 14 in the vicinity of the operator 102, the operation of the insertion portion 20 by the operator 102 and the state of the examination are detected to generate the presentation information 38. The generated presentation information 38, e.g., a sign for moving the operation portion, such as the fan 26A, is wirelessly issued with respect to the monitor 48 and the speaker 50, to which the driver 118 has access at a position distant from the operator 102. Thereby, an efficient and easy inspection environment can be provided.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

The invention claimed is:

1. An information presentation system comprising:
    a tubular system comprising a flexible tubular insertion portion configured to be inserted into an insertion subject by an insertion operation of an operator;
    a storage medium configured to store a plurality of pieces of presentation information configured for display to a patient as a non-operator;
    a non-operator presentation display configured to present the plurality of pieces of presentation information to the non-operator; and
    a state detection circuit configured to detect at least one of a state of the tubular system and a state of the insertion subject;
    a presentation information generation circuit configured to generate specification information which specifies selection and a presentation time of the presentation information to be presented to the non-operator presentation display based on at least one of the states detected by the state detection circuit; and
    a presentation information selection and switching circuit configured to perform switching of the selection and the presentation time of the presentation information read from the storage medium in accordance with the specification information generated by the presentation information circuit, wherein the presentation information generation circuit determines a priority and a duplication possibility, based on comparison between attribute information of newly-acquired presentation information acquired based on a new state detected by the state detection circuit and attribute information of already-presented presentation information; maintains the already-presented presentation information if the priority of the newly-acquired presentation information has a lower priority; generates specification information by adding the newly-acquired presentation information to the already-presented presentation information if the newly-acquired presentation information has a higher priority and the duplication is possible; and completes the presentation of the already-presented presentation information and generates the specification information based on the newly-acquired presentation information if the newly-acquired presentation information has a higher priority and the duplication is not possible.

2. The information presentation system according to claim 1, wherein the presentation information generation circuit is configured to generate specification information that specifies selection and specifies a presentation time of presentation information to be presented to the non-operator presentation display, based on at least one or more states detected by the state detection circuit, and select the presentation information, and switch the presentation period, according to the specification information generated by the presentation information generation circuit.

3. The information presentation system according to claim 2, further comprising a presentation circuit that is configured to interrupt the presentation of the presentation information to the non-operator presentation display.

4. The information presentation system according to claim 2, further comprising:

a presentation information output selection circuit that is configured to select presentation information to be presented to the non-operator and configured to select a presentation method, wherein the presentation information generation circuit generates information that specifies at least one of selection of the presentation information, the presentation period, and a presentation method to the non-operator presentation display, as the specification information, and wherein the presentation information selection and switching circuit is configured to select the selection and configured to select the presentation period of the presentation information, and configured to select the presentation method to the non-operator presentation display, according to the specification information generated by the presentation information generation circuit.

5. The information presentation system according to claim 2, wherein the state detection circuit detects both the state of the tubular system and the state of the insertion subject, wherein the state of the tubular system is detected based on an output of at least one of:

a distal end position detection sensor that is configured to detect a distal end position of the insertion portion; a curved-shape detection sensor that is configured to detect a curved-shape of the insertion portion; an operation amount sensor that is configured to detect an operation amount of an operation of bending the insertion portion; a posture sensor that is configured to detect a posture on a rear end side of the insertion portion; an image sensor provided in the tubular system, and wherein the state of the insertion subject is detected based on an output of at least one of:

an insertion situation observation sensor that is configured to observe an insertion situation; an insertion subject posture sensor that is configured to detect a posture of the insertion subject; a weight-detection sensor that is configured to detect a weight movement of the insertion subject on an examination table; a switching dial configured to be operated by the operator; a tubular system function selection and operation circuit that inputs information for control of the tubular system; an insertion subject state monitoring monitor that is configured to monitor a state of the insertion subject; an insertion amount detection sensor that is configured to detect an insertion amount of the insertion portion into the insertion subject; and a microphone that is configured to detect a sound generated by the insertion subject.

6. The information presentation system according to claim 2, wherein the presentation information generation circuit is configured to select the presentation information to be presented to the non-operator presentation display, from the plurality of pieces of presentation information stored in the storage medium in advance, by determining whether or not the at least one or more states detected by the state detection circuit match a predetermined setting condition.

7. The information presentation system according to claim 2, further comprising a presentation circuit configured to present the presentation information during at least one of the following times: before start of the insertion of the insertion portion; when the insertion portion is inserted into a luminal space of the insertion subject; when insertion difficulties occur during the insertion of the insertion portion; when the insertion of the insertion portion is completed; when entering an examination; during an examination; when a polyp or an affected site is found; when performing a treatment of a close examination of the polyp or the affected site; when performing a treatment; when the tubular system emerges from the insertion subject; and when the insertion of the insertion portion is finished.

8. The information presentation system according to claim 1, further comprising a presentation circuit that is configured to interrupt the presentation of the presentation information to the non-operator presentation display.

9. The information presentation system according to claim 1, wherein the presentation information generation circuit is configured to select presentation information to be displayed in the non-operator presentation display from the group consisting of: an explanation when starting insertion of the insertion portion into the insertion subject, an explanation of a hospital, an explanation of an operator, an explanation of an examination, an explanation of an insertion situation, a sign for requesting a postural change to the insertion subject, an explanation to promote relaxation, an explanation of an examination status or a treatment status, an explanation after completion, and music.

10. The information presentation system according to claim 1, wherein the tubular system is an endoscope comprising an image sensor provided at a distal end of the insertion portion, and a display that displays an image captured by the image sensor, and
wherein the non-operator presentation display includes a monitor separate from the display.

11. The information presentation system according to claim 1, wherein the non-operator presentation display comprises a monitor and a speaker and further at least one of;
a display board that is configured to receive a selection select and also configured to display presentation information by lighting of an indicator light from among a content display of a plurality of pieces of presentation information,
a device comprising a sheet on which contents of the plurality of pieces of presentation information are described, the device configured to move the sheet by a winding/rolling up action to selectively display a content of the presentation information, and
a tactile display.

12. The information presentation system according to claim 1, further comprising an operator presentation display configured to display an observation image to the operator,
wherein the operator presentation display is independent of the non-operator presentation display.

13. The information presentation system according to claim 12, wherein the tubular system further comprises a tubular system driving device controlled in accordance with an operation of the operator and configured to insert the flexible tubular insertion portion into the insertion subject.

14. An information presentation method comprising:
prestoring a plurality of pieces of presentation information configured for display to a patient as a non-operator who is not an operator when a flexible tubular insertion portion is to be inserted into an insertion subject by the operator;
presenting the presentation information to the non-operator via a non-operator presentation display;
detecting at least one of a state of the tubular system and a state of the insertion subject;
generating specification information which specifies selection and a presentation time of the presentation information to be presented to the non-operator presentation display based on at least one of the detected states;
performing switching of the selection and the presentation time of the presentation information read from the storage medium in accordance with the generated specification information;
determining a priority and a duplication possibility, based on comparison between attribute information of newly-acquired presentation information acquired based on a detected new state and attribute information of already-presented presentation information; maintaining the already-presented presentation information if the priority of the acquired presentation information has a lower priority; generating specification information by adding the newly-acquired presentation information to the already-presented presentation information if the newly-acquired presentation information has a higher priority and the duplication is possible; and completing the presentation of the already-presented presentation information and generating the specification information based on the newly-acquired presentation information if the newly-acquired presentation information has a higher priority and the duplication is not possible.

15. The information presentation method according to claim 14, further comprising displaying an observation image to the operator via an operator presentation display independent of the non-operator presentation display.

16. The information presentation system according to claim 15, wherein when the flexible tubular insertion portion is to be into the insertion subject, a tubular system driving device controlled in accordance with an operation of the operator and configured to insert the flexible tubular insertion portion into the insertion subject is used.

* * * * *